(12) United States Patent
Scott et al.

(10) Patent No.: US 10,093,901 B2
(45) Date of Patent: Oct. 9, 2018

(54) USE OF SPECIFIC REGULATORY T-CELLS TO INDUCE IMMUNE TOLERANCE

(71) Applicant: THE HENRY M. JACKSON FOUNDATION FOR THE ADVANCEMENT OF MILITARY MEDICINE, INC., Bethesda, MD (US)

(72) Inventors: David W. Scott, Bethesda, MD (US); Yong Chan Kim, Rockville, MD (US)

(73) Assignee: THE HENRY M. JACKSON FOUNDATION FOR THE ADVANCEMENT OF MILITARY MEDICINE, INC., Bethesda, MD (US)

( * ) Notice: Subject to any disclaimer, the term of this patent is extended or adjusted under 35 U.S.C. 154(b) by 208 days.

(21) Appl. No.: 14/889,962

(22) PCT Filed: May 9, 2014

(86) PCT No.: PCT/US2014/037524
§ 371 (c)(1),
(2) Date: Nov. 9, 2015

(87) PCT Pub. No.: WO2014/183056
PCT Pub. Date: Nov. 13, 2014

(65) Prior Publication Data
US 2016/0194605 A1    Jul. 7, 2016

Related U.S. Application Data

(60) Provisional application No. 61/821,857, filed on May 10, 2013.

(51) Int. Cl.
| | | |
|---|---|---|
| *C12N 5/071* | (2010.01) | |
| *A01N 63/00* | (2006.01) | |
| *C12N 5/0783* | (2010.01) | |
| *A61K 39/00* | (2006.01) | |
| *A61K 35/17* | (2015.01) | |
| *C07K 14/725* | (2006.01) | |

(52) U.S. Cl.
CPC ............ *C12N 5/0637* (2013.01); *A61K 35/17* (2013.01); *A61K 39/0008* (2013.01); *C07K 14/7051* (2013.01); *A61K 2039/5156* (2013.01); *A61K 2039/5158* (2013.01); *A61K 2039/57* (2013.01); *A61K 2039/572* (2013.01); *C12N 2502/11* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 2002/0182670 A1 | 12/2002 | Lollar | |
| 2003/0147865 A1* | 8/2003 | Salomon | ............... A61K 35/17 424/93.21 |
| 2003/0152559 A1 | 8/2003 | Yang et al. | |
| 2012/0027739 A1 | 2/2012 | Jakobsen et al. | |

FOREIGN PATENT DOCUMENTS

| | | |
|---|---|---|
| WO | WO 02/072796 A2 | 9/2002 |
| WO | WO 2005/070090 A2 | 8/2005 |
| WO | WO 2008/095141 A2 | 8/2008 |

OTHER PUBLICATIONS

Ettinger et al., 2010, Haemophilia, vol. 16: 44-55.*
Ettinger et al., 2009, Blood. vol. 114: 1423-1428.*
Rawle et al., 2006, J. Thromb. Haemost, vol. 4: 2172-9.*
Miao et al., 2009, Blood, pp. 1-15.*
Wroblewska et al., "Dangerous liaisons: how the immune system deals with factor VIII," Journal of Thrombosis and Haemostasis, vol. 11, pp. 47-55, Jan. 27, 2013.
Kim et al., "Oligodeoxynucleotides stabilize Helios-expressing Foxp3+ human T regulatory cells during in vitro expansion," Blood, vol. 119, pp. 2810-2818, Mar. 22, 2012.
International Search Report dated Oct. 14, 2014 in application No. PCT/US2014/037524.
Kobayashi et al., "A new cloning and expression system yields and validates TCRs from blood lymphocytes of patients with cancer within 10 days," Nature Medicine, vol. 19, No. 11, Nov. 2013.
Linnemann et al., "High-throughput identification of antigen-specific TCRs by TCR gene capture," Nature Medicine, VJol. 19, No. 11, Nov. 2013.
Kim et al., "Generation and Functional Properties of FVIII-Specific Human T Regulatory Cells: A Novel Approach Using Hemophilia A patient's T Cell Receptors," Blood, vol. 122, No. 21, Nov. 2013.
Brusko et al., "Human Antigen-Specific Regulatory T Cells Generated by T Cell Receptor Gene Transfer," vol. 5, No. 7, p. e11726, Jul. 2010.
Skupsky et al., "B-Cell-Delivered 7, 12, 14, Gene Therapy Induces Functional T Regulatory Cells and Leads to a Loss of Antigen-Specific Effector Cells," Molecular Therapy, vol. 18, No. 8, pp. 1527-1535, Aug. 2010.
Wright et al., "Adoptive therapy with redirected primary regulatory T cells results in antigen-specific suppression of arthritis," Proceedings of the National Academy of Sciences, vol. 106, No. 45, pp. 19078-19083, Nov. 2009.
Supplementary European Search Report dated Jan. 5, 2017 in application No. EP 14 79 4253.
Adair, "Human Tregs Made Antigen Specific by Gene Modification: The Power to Treat Autoimmunity and Antidrug Antibodies with Precision", Frontiers in Immunology (Sep. 2017) vol. B, No. 1117, pp. 1-10.

(Continued)

*Primary Examiner* — Amy E Juedes
(74) *Attorney, Agent, or Firm* — Foley & Lardner LLP

(57) ABSTRACT

The present invention generally relates to the production of antigen-specific T regulatory cells (Tregs). Such cells can be used in therapy to minimize undesirable immune responses such as those observed in autoimmunity and hemophilia and other diseases as well as in the response to protein therapy for genetic diseases. Methods for producing antigen specific Tregs and conditions for preferential expansion of functionally stable, specific Tregs are also provided.

21 Claims, 14 Drawing Sheets

Specification includes a Sequence Listing.

(56) References Cited

OTHER PUBLICATIONS

Daniel-Meshulam et al., "How (specific) Would You Like Your T-Cells Today? Generating T-Cell Therapeutic Function Through TCR-Gene Transfer", Frontiers in Immunology (Jul. 2012), vol. 3, No. 186, pp. 1-12.

* cited by examiner

FIGURE 1D

RQVARVIVFLTLSTLSLAKTTQPISMDSYEGQEVNITCSHNNIATNDYITWYQQFPSQ
GPRFIIQGYKTKVTNEVASLFIPADRKSSTLSLPRVSLSDTAVYYCLVGDAPNSGNTPL
VFGKGTRLSVIANIQNPDPAVYQLRDSKSSDKSVCLFTDFDSQTNVSQSKDSDVYITD
KTVLDMRSMDFKSNSAVAWSNKSDFACANAFNNSIIPEDTFFPSPESSCDVKLVEKSF
ETDTNLNFQNLSVIGFRILLLKVAGFNLLMTLRLWSSRAKRGSGATNFSLLKQAGDV
EENPGPMLLLLLLLGPGSGLGAVVSQHPSRVICKSGTSVKIECRSLDFQATTMFWYR
QFPKKSLMLMATSNEGSKATYEQGVEKDKFLINHASLTLSTLTVTSAQPEDSSFYICS
AHTRANYGYTFGSGTRLTVVEDLNKVFPPEVAVFEPSEAEISHTQKATLVCLATGFFP
DHVELSWWVNGKEVHSGVSTDPQPLKEQPALNDSRYCLSSRLRVSATFWQNPRNHF
RCQVQFYGLSENDEWTQDRAKPVTQIVSAEAWGRADCGFTSVSYQQGVLSATILYEI
LLGKATLYAVLVSALVLMAMVKRKDF (SEQ ID NO:1)

| Chain | TRV | TRD | TRJ | Junction Sequence |
|---|---|---|---|---|
| Alpha | 17*01 | | 40*01 | CATDTTSGTYKYIF |
| Beta | 20-1*01 | 2-1*01 | 2*02 | CSARDLTSGSLNEQFF |

Sequence of TCR is provided from Dr. Kai W. Wucherpfennig

Retroviral insert of Ob2F3 TCR

USE OF SPECIFIC REGULATORY T-CELLS TO INDUCE IMMUNE TOLERANCE

STATEMENT REGARDING FEDERALLY SPONSORED RESEARCH OR DEVELOPMENT

This invention was made with government support under Grant No. HL061883 awarded by the National Institutes of Health (NIH). The government has certain rights in the invention.

FIELD

Described herein are antigen specific T regulatory cells (Tregs). Such cells can be used in therapy to minimize undesirable immune responses, such as those observed in autoimmunity and hemophilia as well as in response to protein therapy for genetic diseases. Methods for producing antigen specific Tregs also are described.

BACKGROUND

T regulatory cells suppress immune responses of other cells. They come in several forms with the most well-understood being those that express CD4, CD25, Foxp3, and Helios ($CD4^+CD25^+$ Tregs). These cells are involved in shutting down immune responses after they have successfully eliminated invading organisms, and in preventing autoimmunity. Methods for expanding non-specific regulatory T cells have been described in the literature. However, because the T cells employed in those methods were non-specific, the activity of such cells could be immunosuppressive for responses to pathogenic infections and cancer, where an immune response would be desirable.

There currently exists a need for effective therapies to minimize or eliminate the undesirable immune response to self components that is the underlying cause of autoimmune disorders, including type 1 diabetes, uveitis and multiple sclerosis, and the unfavorable response to treatment of genetic diseases like hemophilia and Pompe's with biotherapeutics.

SUMMARY

In accordance with some embodiments, there is provided a method for producing antigen specific T regulatory cells comprising transducing T cells with an expression vector comprising a nucleotide sequence encoding a T cell receptor that specifically recognizes the antigen, and expanding the transduced T cells ex vivo. In some embodiments, transducing the T cells comprises transducing HLA matched restricted natural T regulatory cells. In some embodiments, the transducing comprises transducing cells with an amphotrophic packaging retrovirus. In some embodiments, the T cells are obtained from a donor's buffy coat prior to being transduced.

In accordance with any of these embodiments, the antigen is selected from the group consisting of the C2 domain of human clotting factor VIII and antigens associated with multiple sclerosis, such as myelin basic protein or myelin oligodendrocyte glycoprotein (MBP, MOG), diabetes (e.g., GAD65), or uveitis (S-antigen). In some embodiments, the antigen is a human clotting factor, such as factor VIII in which case the T cell receptor may have the amino acid sequence of SEQ ID NO:1. In some embodiments, the antigen is involved in a subject's reaction to biotherapeutics in genetic diseases like Pompe's and hemophilia.

In accordance with any of these embodiments, the cells may be subjected to a stimulation step prior to transduction, and/or an expansion step following transduction.

Also provided is a method for expanding T regulatory cells and/or T effector cells transduced with a T cell receptor-encoding sequence, comprising culturing the cells in IL-2 containing RPMI1640 media with 10% fetal bovine serum. In some embodiments, the culturing is effected for up to 4 days.

Also provided is a method for expanding T regulatory cells transduced with a T cell receptor-encoding sequence, comprising comprising culturing the cells in the presence of the specific antigen recognized by the T cell receptor and oligodeoxynucleotides, and optionally further in the presence of irradiated DR1 HLA-typed peripheral blood mononuclear cells and IL2. In some embodiments, the culturing is effected for about 21 days.

Also provided are antigen specific T regulatory cells prepared by any method described herein.

Also provided are methods of reducing an immune response to an antigen, comprising administering to a subject in need thereof a composition comprising an antigen specific T regulatory cell as described herein that is specific to the antigen. In some embodiments, the subject is suffering from hemophelia, multiple sclerosis, diabetes or uveitis. In some embodiments, the subject is receiving biotherapeutics for a genetic disease such as Pompe's or hemophilia.

Figures 1A, 1B, 1C:
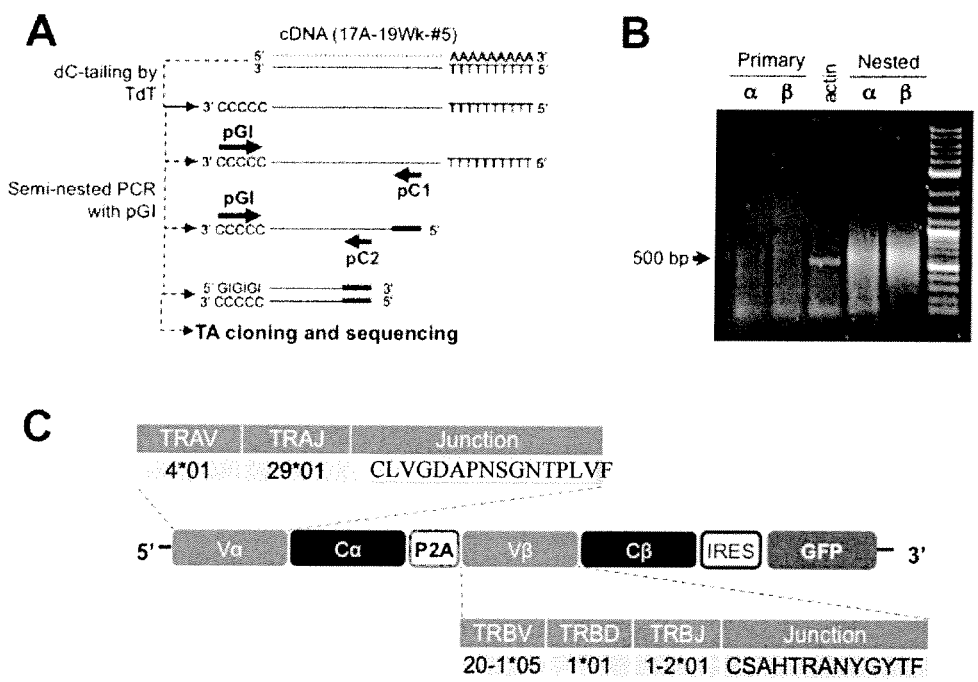
FIG. 1. Identification and retroviral expression of a FVIII-2191-2220-specific TCR in primary CD4 T cells (A) Scheme of FVIII-2191-2220-specific TCR cloning from a hemophilia A subject's T-cell clone. The cloning procedure is described in Materials and Methods. Briefly, to amplify TCR cDNA from the clone, poly C oligonucleotide was linked onto the 3' terminus of total cDNAs by terminal deoxynucleotidyl transferase (TdT). The variable region was amplified using semi-nested PCR with a poly GI primer and two reverse primers (pC1 and pC2) corresponding to two different 5' upstream coding regions of the α and β chain constant regions. The figure discloses "TTTTTTTTTT" as SEQ ID NO: 8.

(B) Amplification of V regions of the 17195TCR using semi-nested PCR. Primary amplification and nested amplification were carried out with pC1 and pC2 (FIG. 1A). PGI was commonly used as the forward primer for the primary and nested PCR step. Bold arrows indicate the predicted sizes of the amplified Vα and Vβ PCR products.

(C) Retroviral expression construct of the FVIII-2191-2220-specific TCR. To build the FVIII-2191-2220-specific TCR, the variable regions (Vα and Vβ) from the FVIII-2191-2220-specific T effector clone were combined with human constant regions (Cα and Cβ) extracted from the NCBI database. To produce the individual α and β TCR chains from a single transcript, a P2A cleavage peptide was inserted between the α and β chain sequences. Expression of the GFP reporter is controlled by IRES, which is located downstream of the TCR construct. The figure discloses SEQ ID NOS 9 and 10, respectively, in order of appearance.

(D) Amino acid sequence of a FVIII C2-specific human T cell receptor (TCR17195).

Figure 2:
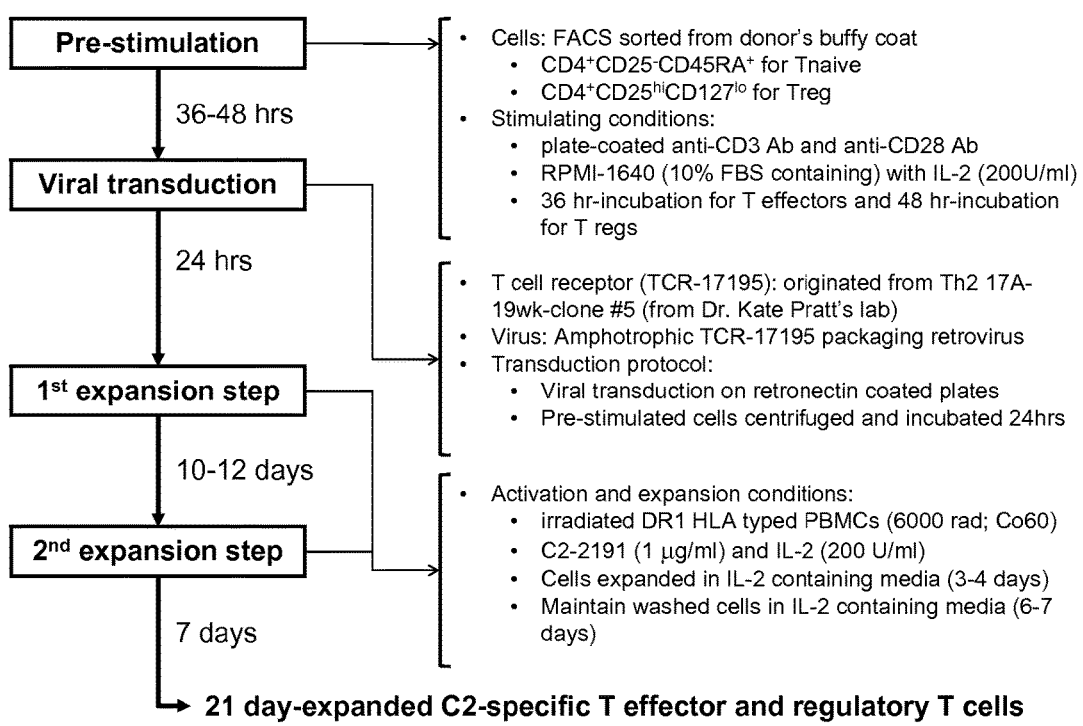

FIG. 2. Flow chart depicting a protocol for producing FVIII C2-specific human regulatory T cells and effector T cells. To produce FVIII C2-specific T effector cells, naïve human T cells ($CD4^+CD25^-CD127^+CD45RA^+$) were isolated by FACS sorting (FACSAria, BIC, USUHS) from healthy donor's buffy coat. The cells were pre-stimulated with plate-coated anti-CD3e antibody and plate-coated anti-CD28 antibody for 48 hrs. Then, the cells were transduced with amphotropic TCR-17195-IRES-GFP-containing retroviral culture supernatant in retronectin-coated plates (to express the TCR from a patient clone reactive to FVIII). The transduced cells were expanded in IL2-containing RPMI1640/10% FBS for 4 days. To confirm activation of T cells by FVIII C2, the expanded effector T cells in which TCR17195 was expressed (Teff-17195) were cultured for 4 days with gamma-irradiated DR1-HLA typed PBMCs (6000 rad by Co60) in the presence of pOVA (negative control), pFVIII C2, or soluble anti-CD3e antibody. To produce TCR17195-expressing T regulatory cell (Treg-17195), human Tregs ($CD4^+CD25^{hi}CD127^{lo}$) were isolated from healthy donor's buffy coat. Pre-stimulation, retroviral transduction, and expansion of Treg-17195 was done as described for T effector cells. To confirm C2-specific Treg activation through TCR17195, expanded Treg-17195 cells were co-cultured with gamma-irradiated DR1-HLA typed PBMCs (6000 rad by Co60) for 24 hrs in the presence of pOVA, pFVIII C2, or soluble anti-CD3e antibody.

FIG. 3. Activation of 17195 T effectors by FVIII-2191-2220

(A) Proliferation of 17195TCR-transduced CD4 T cells with FVIII-2191-2220. Pre-stimulated primary CD4 T cells were transduced with 17195TCR or with a mock vector and maintained for 10 days in culture media supplemented with IL-2. For proliferation assays, cells were labeled with cell proliferation dye (eFluor 450) and then re-activated with irradiated DR1-PBMCs plus peptide FVIII-2191-2220 (0.5 µg/ml), pOVA (0.5 µg/ml), or anti-CD3ε antibody (0.5 µg/ml) for 4 days. Cell proliferation was measured by flow cytometry using a standard dye dilution assay. Representative results are shown for CD4 cells from two different donors that were transduced with 17195TCR.

(B) Staining of transduced, expanded $GFP^+$ 17195 T effectors shown in (A) using PE-labeled DR1 tetramers loaded with FVIII-2191-2220.

(C) Proliferation of $GFP^-$ and $GFP^+$ T cell effectors stimulated with OVA peptide, FVIII-2191-2220 or anti-CD3ε antibody. Transduced T effectors ($2\times10^6$/well) were stimulated using irradiated DR1-APCs (Responder:Stimulator=1:5) as in (A). After culturing for 10 days, The cells were harvested and, viable $GFP^-$ and $GFP^+$ CD4 cells were counted using flow cytometry.

(D) Retroviral expression of 17195 TCR in CD4 T naïve and CD4 Treg cells. Naïve T cells were pre-stimulated in plate-bound anti-CD3 antibody and anti-CD28 antibody for 48 hrs. Then, these cells were transduced in virus-coated plate for 24 hrs. Expression of GFP and staining with FVIII peptide/DR1 tetramer was performed by FACS analysis at 3 days after transduction of 17195TCR.

(E) Cell surface expression of 17195 TCR in transduced T cells (10 day-cultured). Expression of retroviral 17195 TCR was measured by flow cytometry with anti-Vβ2 versus GFP.

(F) FVIII peptide-specific induction of Treg-specific surface markers in transduced Tregs. Two week-expanded mock and 17195 Tregs (transduction followed as in FIG. 2A and then expansion with irradiated DR1 PBMCs in the presence of FVIII peptide) were re-activated for 48 hrs with irradiated APCs and FVIII peptide (0.5 g/ml) in the presence of IL-2 (200 U/ml). Histograms show the relative expression of LAP, GARP, and GITR in GFP-positive transduced population.

Figure 4:
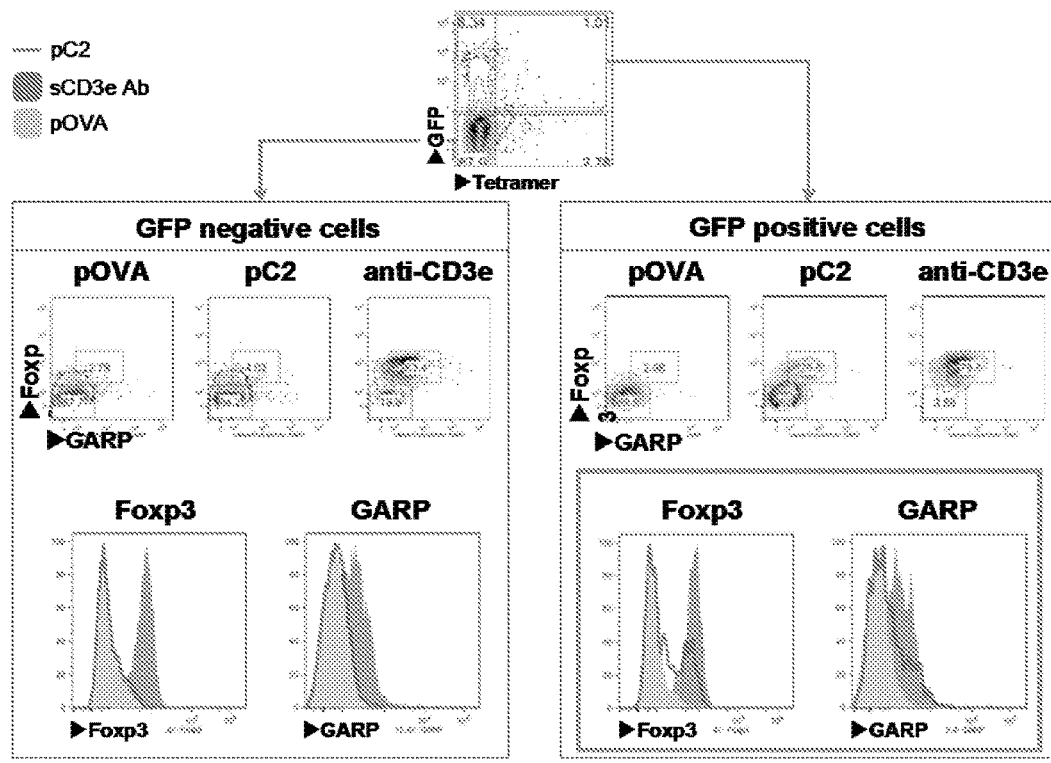

FIG. 4. Data showing that TCR17195 activates transduced human Tregs in an FVIII C2-specific manner. To confirm C2-specific Treg activation through TCR17195, expanded Treg-17195 cells were co-cultured with gamma-irradiated DR1-HLA typed PBMCs (6000 rad by Co60) for 24 hrs in the presence of pOVA, pFVIII C2, or soluble anti-CD3e antibody. Foxp3 and GARP (glycoprotein A repetitions predominant, LRRC32) staining was then done on fixed, co-cultured cells. Foxp3 and GARP are transiently induced at the early stage (24-48 hrs) of activated Tregs. In GFP negative population, the induction of Foxp3 and Helios was shown only in the anti-CD3e Ab stimulation group and pC2-mediated stimulation did not give any induction of Foxp3 and Helios (dot plots and histograms in left box). In GFP positive cells (expressing the TCR), stimulation by C2 induces expression of Foxp3 and Helios in a portion of cells as well as stimulation by CD3e.

FIG. 5. Optimized ex vivo expansion of 17195TCR-Tregs with FVIII-2191-2220 plus oligodeoxynucleotides (A) FVIII-2191-2220-specific enrichment of transduced $Foxp3^+Helios^+$ Tregs via long-term expansion. After a $2^{nd}$ round of expansion (described in FIG. 10), the CD4 T cells were stained using DR1 tetramers loaded with FVIII-2191-2220 (top dot plots). Expression of Foxp3 and Helios in gated $CD4^+GFP^+$ population were also evaluated with intracellular staining (bottom contour plots).

(B) Comparison of FVIII-2191-2220-specificity and $Fox3^+Helios^+$ phenotypes for short-term and long-term expanded 17195TCR-Tregs. First-round expanded (Exp) cells ($1^{st}$ Exp) were harvested 8 days after viral transduction and second-round expanded cells ($2^{nd}$ Exp) were harvested 16 days after transduction. Tetramer staining (to determine FVIII-2191-2220 specificity) and intracellular FACS staining (to quantify Foxp3 and Helios expression) were performed as in FIG. 5A. Representative data from one of two experiments are shown.

(C) Plasticity of long-term expanded 17195TCR-Tregs and Treg phenotype stability induced by antigen. Second-round expanded 17195TCR-transduced Tregs were rested for 3-days of culture without IL-2 and then re-stimulated for 4 hrs with PMA and ionomycin in the presence of Golgi-block reagent. Intracellular IFNγ (top contour plots and graph) and IL-2 (bottom contour plots and graph) production were measured by FACs analysis.

(D) DNA methylation of TSDR in long-term expanded 17195TCR Tregs with FVIII-2191-2220 plus ODN. To analyze DNA methylation in the TSDR, mock-transduced and 17195TCR-transduced Tregs were expanded with anti-CD3ε antibody or FVIII-2191-2220 in the presence of ODN, as in FIG. 4A. TSDR is an unmethylated CpGs-enriched region within Foxp3 genome of natural Treg. Heat map analysis shows methylation status of specific nine out of total eleven CpGs. The histogram summarized the mean percent methylation of the 9 TSDR CpGs in 17195TCR-transduced Tregs with FVIII 2191-2220/ODN stimulation vs. anti-CD3ε antibody stimulation condition.

Figures 6A, 6B:
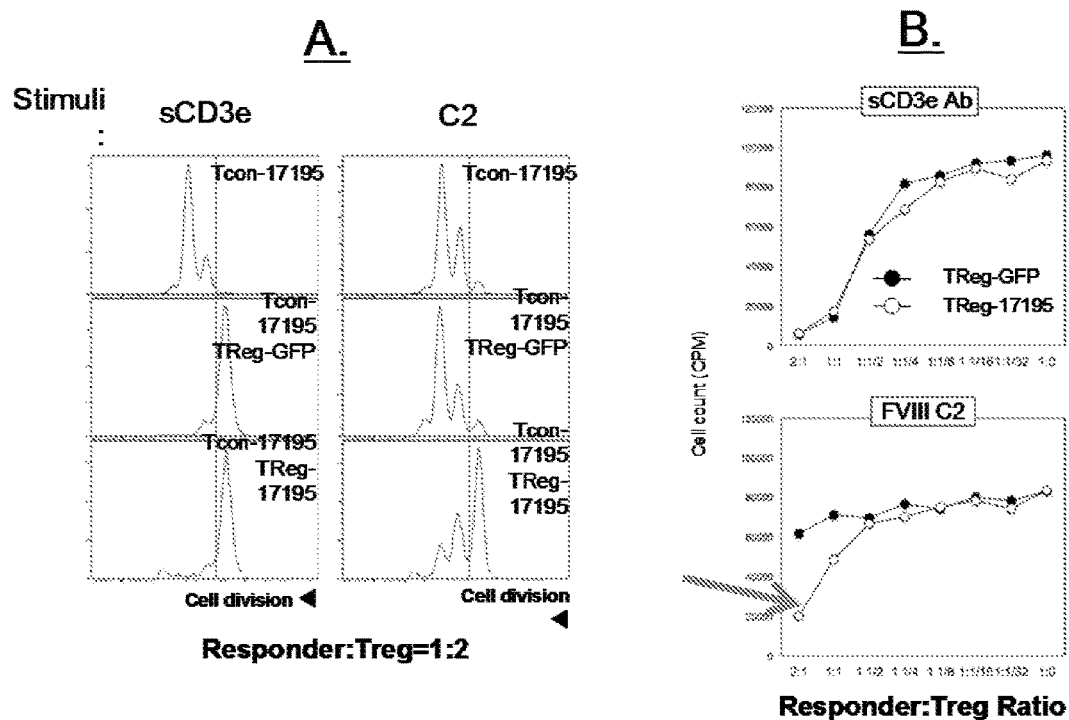

FIG. 6. Data illustrating C2-specific immunosuppression by Tregs expressing TCR17195 in vitro. For the immunosuppression assay, naïve T effector cells and Tregs were prepared as in FIGS. 2-4. T naïve cells were expanded with C2 and irradiated antigen-presenting cells (APC) after viral transduction of TCR17195 for 14 days. The expanded T effector-17195 population was used as responder cells. To monitor cell division of GFP positive cells, responders were labeled with the Cell Proliferation Dye-eFluor450 (CPD450). Tregs cells were transduced with mock virus or TCR17195, then were expanded for 14 days with anti-CD3ε antibody or pC2 peptide. In the co-culture, the ratio of Responders to Stimulators was fixed at 1:1 and the amount of Tregs was varied as indicated. Cell mixtures were cultured with anti-CD3e antibody or pC2 for 2 days (A) or 4 days (B) without IL-2 addition. A. C2-specific inhibition of division of the proliferation dye CPD450 labeled GFP+ responders by Treg-17195. Left histograms show cell division of labeled responder co-cultured with Treg-GFP or Treg-17195 in the presence of anti-CD3e antibody and irradiated APCs. Co-culture in the presence of pC2 is shown in right histograms. B. C2-specific immunosuppression by Treg-17195. To confirm and measure cell growth in mixed culture, [$^3$H]-thymidine was added at 18 hrs before harvest, with similar results.

(C) Suppression of FVIII-specific cytokine secretion by 17195TCR-Tregs. Four week-expanded mock-transduced Tregs or 17195TCR-Tregs were mixed with 17195TCR-T effectors (responders) at the indicated ratios with γ-irradiated DR1-PBMCs and rFVIII (0.2 μg/ml) and cultured for 36 hrs without IL-2. Cytokines in culture media were measured using a human Th1, Th2, Th17 CBA kit (BD Bioscience). The quality of the mock-transduced and 17195TCR-transduced Tregs was evaluated by measuring their GFP expression (left panels) and the expression of Foxp3 and Helios in the GFP+ cells (right panels). Raw MFI data from the CBA assays were converted to cytokine concentrations according to standard curves generated for each experiment. Data are presented as mean±SD.

Figures 7A, 7B, 7C, 7D, 7E:
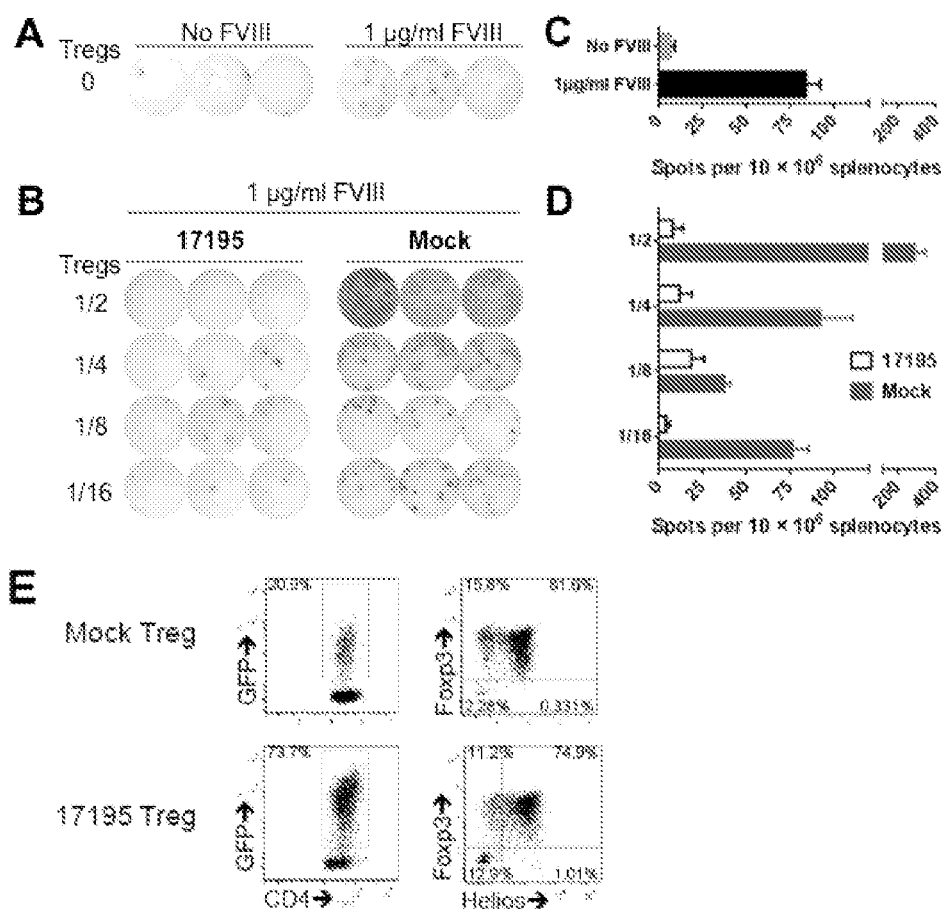

FIG. 7. In vitro suppression of anti-FVIII antibody production by engineered FVIII-specific human Tregs Pooled splenocytes from two immunized DR1/E16-FVIII-KO mice were used as T-responders. In a T25 flask, 1×10$^7$ splenocytes were co-cultured with 17195TCR-transduced or mock-transduced Tregs at different ratios in the absence/presence of 1 μg/ml rFVIII. After 6 days in culture, FVIII-specific antibody secreting cells (ASC) were detected using an ELISPOT assay as described in Methods.

(A) FVIII-specific ASC detected in splenocyte cultures that contained no TCR- or mock-transduced Tregs.

(B) FVIII-specific ASCs detected in splenocytes co-cultured with various ratios of 17195TCR-transduced or mock-transduced Tregs. Co-culture with 17195TCR-Tregs profoundly inhibited anti-FVIII ASC formation, even with responder to suppressor ratios as low as 1:0.0625 (1/16). The histograms in (C) and (D) summarize the ELISPOT data in (A) and (B), respectively. Data are presented as mean±SEM. (E) The quality of the Tregs used in these experiments was evaluated by measuring their GFP expression (left panels) and the expression of Foxp3 and Helios in the GFP+ cells (right panels).

Figure 8:

FIG. 8. Identification and retroviral expression of a Ob2.F3-specific TCR in primary CD4 T cells. Retroviral expression construct of the Ob2.F3-specific TCR.

Figure 9:
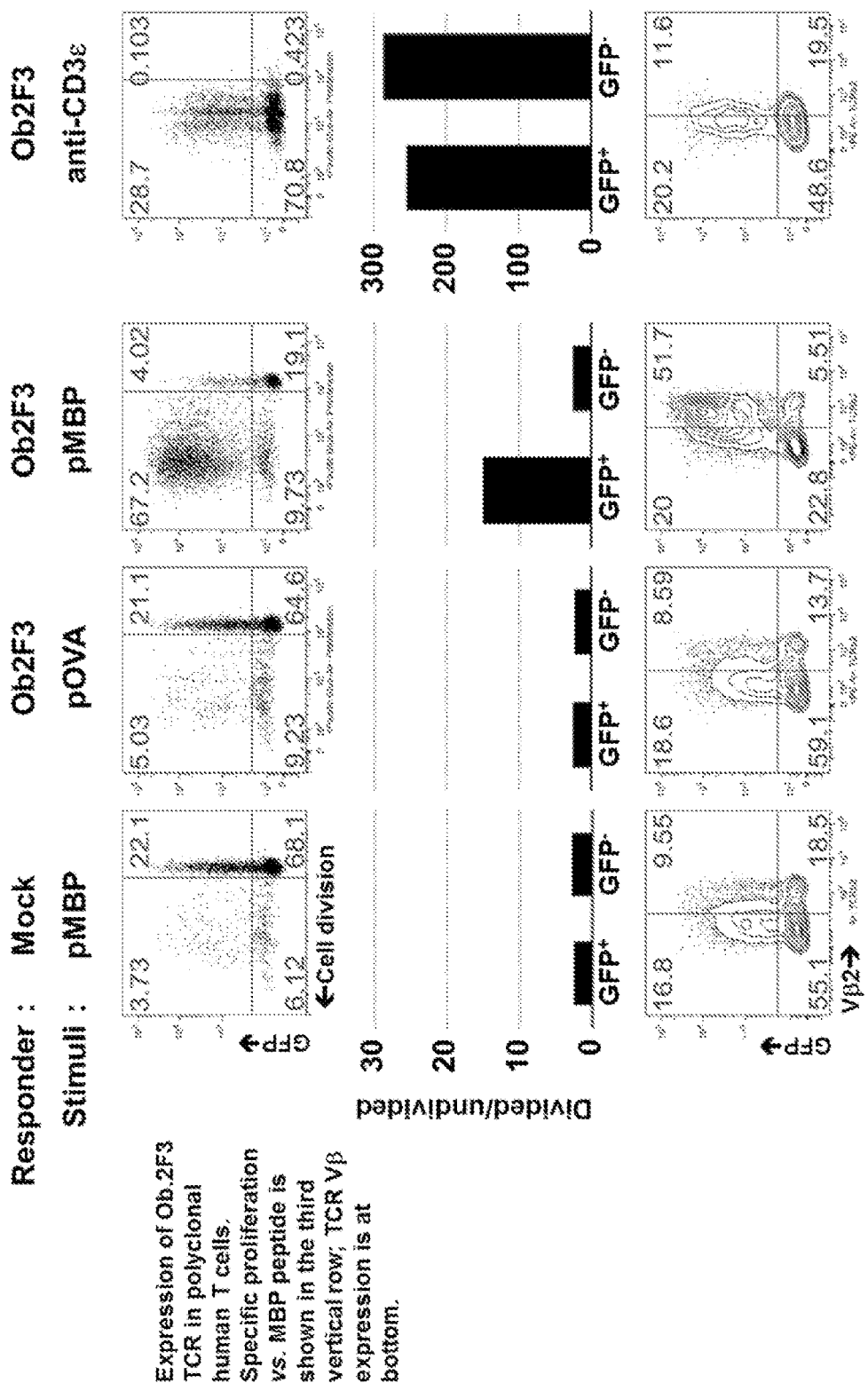

FIG. 9. Expression of Ob.2F3 TCR in polyclonal human T cells. Specific proliferation vs. MBP peptide is shown in the third vertical column; TCR Vβ expression is in the bottom row.

Figure 10:
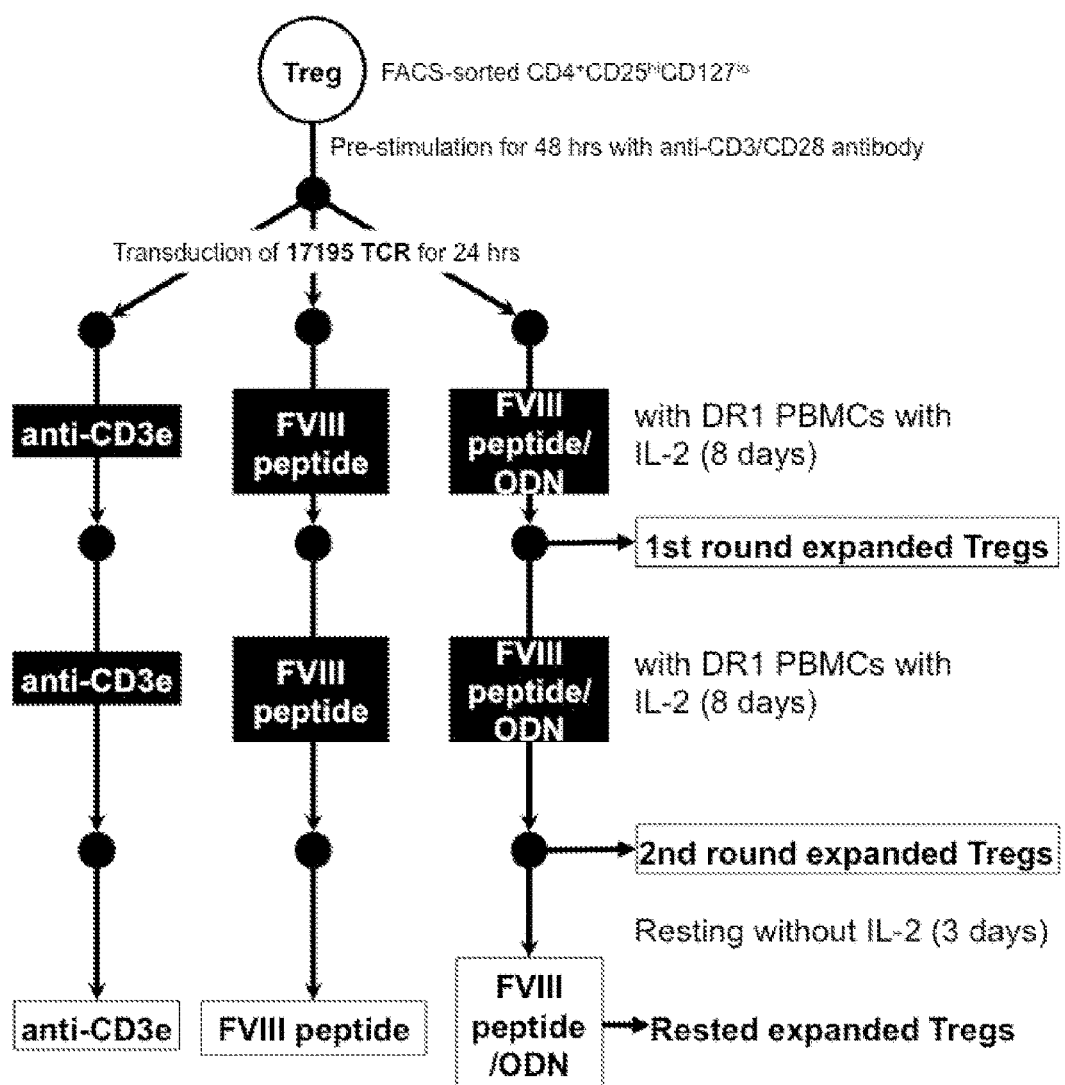

FIG. 10. A diagram of three ex vivo culture conditions for long-term expansion of functionally stable specific Tregs.

Pre-stimulated Treg cells (CD4+CD25hiCD127lo) were transduced with retroviral 17195 TCR and then 1st round expanded for 8-10 days with three different stimuli: anti-CD3e antibody, FVIII peptide, or FVIII peptide plus oligonucleotide (FVIII peptide/ODN) in the presence of irradiated DR1 PBMCs and IL-2 (200 U/ml). For 2nd round expansion culture, the cells were rested in the media without IL-2 for 48-72 hrs. The stimulating and culturing condition for 2nd expansion was identical with 1st expansion. After 2nd expansion, the expanded cells were rested for 48 hrs in the absence of IL-2 for further experiments. To monitor the quality of each grouped 17195 Tregs, FVIII peptide/DR1 tetramer staining and intracellular staining of Foxp3 and Helios were performed every 5 days during the expansion culture.

Figure 11:
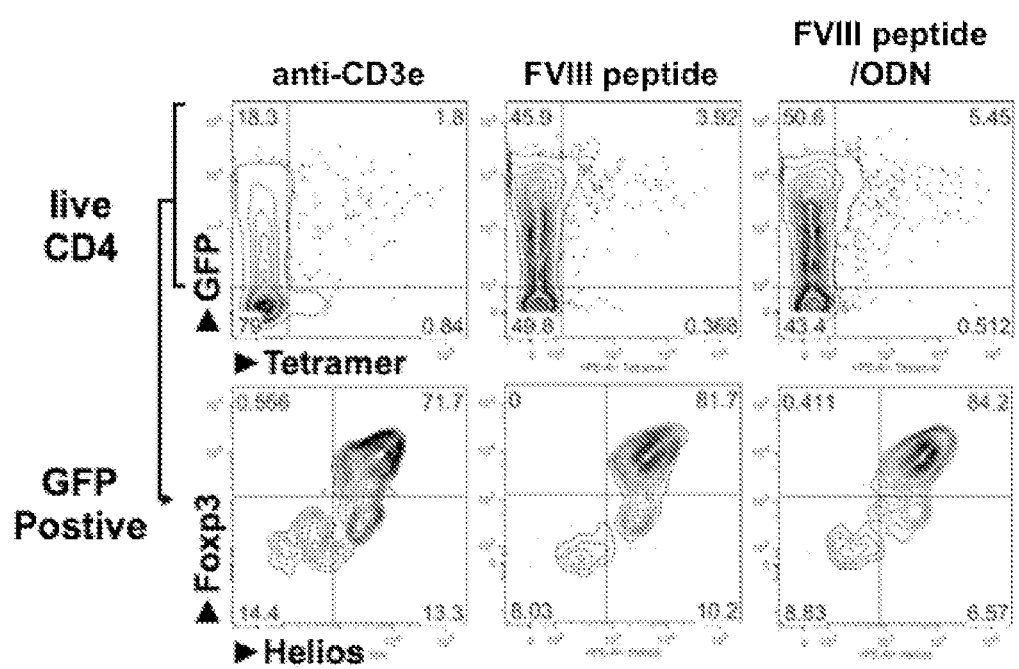

FIG. 11. FVIII peptide-specific enrichment of transduced Foxp3+Helios+ Tregs in short-term expansion culture (1st round expansion).

DETAILED DESCRIPTION

Described herein are methods of producing specific human T regulatory cells (Tregs), useful, for example, to reduce undesirable immune responses in conditions such as autoimmunity, including hemophilia, type 1 diabetes, uveitis and multiple sclerosis, as well as in the response to protein therapy for genetic diseases. As used herein the term "specific" Tregs designates Tregs that respond to a specific antigen and inhibit effector T cells that are reactive to a specific antigen.

Specific embodiments of the methods are illustrated as follows: T cell receptors (TCR) from a patient with an autoimmune disease (such as, for example, a hemophilia A patient) are cloned. TCRs can be cloned according to procedures known in the art, including those described in *Nature Medicine*, 19(11) 1534-41 (2013) and *Nature Medicine*, 19(11) 1542-46 (2013). Stimulated patient's polyclonal T cells are transduced with the TCRs, thus rendering the expanded cells antigen specific. When the polyclonal Tregs, isolated from peripheral blood, are stimulated under conditions that lead to non-specific Tregs, the cells can then be transduced to become antigen-specific Tregs, capable of specifically suppressing the undesirable immune response to the antigen.

T cells previously have been rendered specific for cancer antigens (CAR's) to specifically destroy cancer cells (turn on immunity). However, the methods described herein produce specific Tregs to modulate (turn off) undesirable immune responses, e.g., to reduce an immune response. The present inventors have now obtained definitive evidence that specific Tregs can be produced using the methods described herein, and that the resulting Tregs are functionally active to inhibit effector T cells that are reactive to a specific antigen (e.g., an FVIII peptide). By expressing a specific TCR directed to a specific antigen, (e.g., human clotting factor VIII, MBP, MOG, GAD65, S-Antigen, or other target), a patient's Tregs can be made specific and used for immunotherapy of the associated disease.

In addition, the methods described herein provide for the first time a protocol for preferential expansion of functionally stable, specific Tregs using specific antigen and oligonucleotide components. The methods therefore are useful for producing Tregsin a cellular therapy to treat, for example, hemophilia patients who are prone to making antibodies against FVIII. Further, the methods can be applied to other diseases associated with undesirable immune responses, such as type I diabetes, multiple sclerosis, uveitis, and other conditions of autoimmunity, or undesireable immune response to protein therapy.

Thus, described herein are methods for developing antigen-specific T regulatory cells (Tregs), which can be used to treat or minimize unwanted immune responses, such as those that occur in autoimmune diseases and in protein therapy for genetic diseases. Conditions for preferential expansion of functionally stable, specific Tregs using specific antigen and oligonucleotide components also are described.

In accordance with one aspect, there is provided a method for producing antigen specific T regulatory cells comprising transducing T cells with an expression vector comprising a nucleotide sequence encoding a T cell receptor that specifically recognizes the antigen, and expanding the transduced T cells ex vivo. In some embodiments, the T cells are expanded ex vivo to obtain a greater number of functional Tregs and without experiencing functional loss.

In some embodiments, the T cells are obtained from a donor's buffy coat by, for example, FACS sorting (FACSAria, BIC, USUHS) CD4+CD25-CD45RA+ for T naïve cells and CD4+CD25$^{hi}$CD127$^{lo}$ for Treg cells, prior to being transduced. In some embodiments a pre-stimulation step precedes the transduction step. For example, cells may be pre-stimulated with plate-coated anti-CD3ε antibody and plate-coated anti-CD28 antibody for 36 to 48 hours.

In accordance with any of the foregoing embodiments, transducing the T cells may comprise transducing HLA DR1 restricted natural T regulatory cells and/or effector T cells. In some embodiments, the transducing comprises transducing pre-stimulated cells with an amphotrophic packaging retrovirus containing a sequencing encoding a T cell receptor. In specific embodiments, the T cell receptor is specific for clotting factor FVIII. In further specific embodiments, the cells are transduced with an amphotrophic TCR-17195 packaging retrovirus designated TCR-17195-IRES-GFP (i.e., a retroviral construct comprising a sequence encoding the TCR-17195 linked with green fluorescent protein (GFP) expression via intra ribosome entry site (IRES)).

In accordance with any of the foregoing embodiments, the transduction protocol may involve transduction with retroviral culture supernatant in retronectin-coated plates.

In some embodiments, after transduction by viral particles, expressed TCR can be detected flow cytometry based on GFP expression.

In specific embodiments, expansion of transduced Treg or T effector cells may be carried out in IL-2 containing RPMI1640 media with 10% fetal bovine serum (FBS) for up to 4 days.

In specific embodiments, the expansion step of specific Tregs is conducted in accordance with oligonucleotide technology as disclosed in Kim et al., "Oligodeoxynucleotides stabilize Helios-expressing Foxp3+ human T regulatory cells during in vitro expansion," Blood 2012 Mar. 22; 119(12):2810-8. doi: 10.1182/blood-2011-09-377895. Epub 2012 Jan. 31, incorporated herein by reference in its entirety. For example, a 25mer DNA oligonucleotide of random composition may be added during the expansion of Tregs in vitro to prolong stabilization of the Foxp3$^+$Helios$^+$ subpopulation and to yield a population particularly suitable for use in cellular biotherapy. In the oligonucleotide treatment protocol in the long term expansion of antigen-specific Tregs, expanded Tregs express almost the same level of Foxp3 and Helios as freshly isolated Tregs. Moreover, oligonucleotide treatment maintains demethylation status of Treg-specific demethylation region (TSDR) in the expanded Tregs.

In some embodiments the T cells are subjected to a stimulation step prior to being transduced, and then subjected to an expansion step after transduction.

In some embodiments, the antigen for which the antigen-specific T regulatory cells and/or T effector cells are specific is selected from the group consisting of the C2 domain of human clotting factor VIII (FVIII) or an antigen associated with multiple sclerosis, type I diabetes, uveitis, or other diseases.

An exemplary sequence of a FVIII C2-specific human T cell receptor (TCR17195) is the 620 amino acid sequence of SEQ ID NO:1 below:

(SEQ ID NO: 1)
RQVARVIVFLTLSTLSLAKTTQPISMDSYEGQEVNITCSHNNIATNDYIT

WYQQFPSQGPRFIIQGYKTKVTNEVASLFIPADRKSSTLSLPRVSLSDTA

VYYCLVGDAPNSGNTPLVFGKGTRLSVIANIQNPDPAVYQLRDSKSSDKS

VCLFTDFDSQTNVSQSKDSDVYITDKTVLDMRSMDFKSNSAVAWSNKSDF

ACANAFNNSIIPEDTFFPSPESSCDVKLVEKSFETDTNLNFQNLSVIGFR

ILLLKVAGFNLLMTLRLWSSRAKRGSGATNFSLLKQAGDVEENPGPMLLL

LLLLGPGSGLGAVVSQHPSRVICKSGTSVKIECRSLDFQATTMFWYRQFP

KKSLMLMATSNEGSKATYEQGVEKDKFLINHASLTLSTLTVTSAQPEDSS

FYICSAHTRANYGYTFGSGTRLTVVEDLNKVFPPEVAVFEPSEAEISHTQ

KATLVCLATGFFPDHVELSWWVNGKEVHSGVSTDPQPLKEQPALNDSRYC

LSSRLRVSATFWQNPRNHFRCQVQFYGLSENDEWTQDRAKPVTQIVSAEA

WGRADCGFTSVSYQQGVLSATILYEILLGKATLYAVLVSALVLMAMVKRK

DF

In another embodiment, the antigen for which the antigen-specific T regulatory cells and/or T effector cells are specific is selected is an antigen associated with multiple sclerosis. An exemplary sequence of a Ob.2F3-specific human T cell receptor is the amino acid sequence of SEQ ID NO:2 below:

ETLLGVSLVILWLQLARVNSQQGEEDPQALSIQEGENATMNCSYKTSINN

LQWYRQNSGRGLVHLILIRSNEREKHSGRLRVTLDTSKKSSSLLITASRA

ADTASYFCATDTTSGTYKYIFGTGTRLKVLANIQNPDPAVYQLRDSKSSD

KSVCLFTDFDSQTNVSQSKDSDVYITDKTVLDMRSMDFKSNSAVAWSNKS

DFACANAFNNSIIPEDTFFPSPESSCDVKLVEKSFETDTNLNFQNLSVIG

FRILLLKVAGFNLLMTLRLWSSRAKRGSGATNFSLLKQAGDVEENPGPML

LLLLLLGPGISLLLPGSLAGSGLGAVVSQHPSWVICKSGTSVKIECRSLD

FQATTMFWYRQFPKQSLMLMATSNEGSKATYEQGVEKDKFLINHASLTLS

TLTVTSAHPEDSSFYICSARDLTSGSLNEQFFGPGTRLTVLEDLNKVFPP

EVAVFEPSEAEISHTQKATLVCLATGFFPDHVELSWWVNGKEVHSGVSTD

PQPLKEQPALNDSRYCLSSRLRVSATFWQNPRNHFRCQVQFYGLSENDEW

TQDRAKPVTQIVSAEAWGRADCGFTSVSYQQGVLSATILYEILLGKATLY

AVLVSALVLMAMVKRKDF

Also described herein is a protocol for preferential expansion of functionally stable, specific Tregs using specific antigen and, optionally, oligonucleotide components as described above. This protocol comprises gamma-irradiated DR1-HLA typed PBMCs as antigen presenting cells (6000 rad by Co60) and recombinant IL2 as a growth factor in the media.

Examples

Identification of FVIII-Specific TCR

The cloning strategy for the FVIII-specific TCR from a hemophilia A T effector clone is shown in FIG. 1A. Briefly, cDNA from clone 17A-19wk-5[2,3] (abbreviated 17195TCR) was tagged with a poly-C tail using a terminal transferase reaction. The V regions were then amplified using a common poly-GI forward primer (pGI: 5'-CACCGGGIIGGGI-IGGGII-3' (SEQ ID NO: 3)) and two different sets of human constant region-specific reverse primers (pC1 and pC2: pCa1, 5'-AGTCAGATTTGTTGCTCCAGGCC-3' (SEQ ID NO: 4); pCb1, 5'-TTCACCCACCAGCTCAGCTCC-3' (SEQ ID NO: 5); pCa2, 5'-ATACGCGTTCTCTCAGCTG-GTACACGG-3' (SEQ ID NO: 6); pCb2, 5'-ATACGCGTA-GATCTCTGCTTCTGATGGC-3' (SEQ ID NO: 7)). After a second round of PCR with these primers, amplified V regions (500-600 base pairs) were cloned into a TA cloning vector (Invitrogen) (FIG. 1B). Insertion of PCR product was confirmed by restriction enzyme digestion of plasmid DNA. Extracted individual sequences were nBlast-matched with reference database sequences from the International ImMunoGeneTics (IMGT) and NCBI. Once the identified α and β chain V regions were identified, the TCR of clone 17195TCR was constructed utilizing the human TCR constant region C region reference sequence. To incorporate the α and β sequences, the α and β chain regions were connected by a P2A peptide linker[4] to create a single construct (FIG. 1C), and cDNA for green fluorescent protein (GFP) was inserted downstream of the TCR coding region separated by an internal ribosomal entry site (IRES). The re-designed retroviral 17195TCR construct was synthesized by GenScript USA, Inc. (Piscataway, N.J.). Retrovirus was produced using a Phoenix-Ampho packaging system.

Isolation, Transduction, and Expansion of TCR-Transduced T Effectors and Tregs Buffy-coat fractions from healthy 20-70-year-old males were provided by the Department of Transfusion Medicine at the National Institutes of Health (NIH) or purchased from the American Red Cross. All procedures were approved by the USUHS Institutional Review Board, and all blood donors provided written informed consent in accordance with the Declaration of Helsinki. To obtain CD4 T-naïve and Treg cells, peripheral blood mononuclear cells (PBMC) were isolated from buffy coats by ficoll separation (Ficoll-Paque™ Plus, GE Healthcare). CD4 T cells were enriched by positive selection with MACS (Miltenyi Biotech, Auburn, Calif.). Naïve CD4 T cells ($CD4^+CD25^-CD127^+CD45RA^+$) and Tregs ($CD4^+CD25^{hi}CD127^{lo}$) were then sorted on a FACSAria (BD Biosciences).

For transduction of 17195TCR, T-naïve cells or Tregs ($2\times10^5$/ml) were stimulated with plate-coated anti-CD3ε (5 µg/ml) and anti-CD28 antibodies (2 µg/ml) for 48-72 hrs plus recombinant human IL-2 (200 U/ml). Stimulated cells were transferred into 17195TCR viral particle-coated, retronectin (10 µg/ml)-pretreated plates and incubated for 24 hrs. After transduction, the cells were expanded for 3-5 weeks with 6000r gamma-irradiated HLA-DRB1*01:01 (abbreviated hereafter as DR1) PBMCs and peptide FVIII-2191-2220 (0.2-0.5 µg/ml) plus IL-2 (200 U/ml). Irradiated PBMCs (PBMC:T cells=2:1) and FVIII-2191-2220 (0.5 µg/ml) were added to the culture every 2 weeks. Expanded 17195TCR-effectors and 17195TCR-Tregs were rested in the media (RPMI1640 supplemented with 10% fetal bovine serum (FBS), 1% human AB serum, 1× Glutamax, and antibiotics) for 48-72 hrs.

Intracellular Staining for Foxp3, Helios, and Cytokines

Rested cells were re-stimulated with phorbol myristate acetate (PMA; 50 ng/ml) and Ionomycin (1 µg/ml) for 4 hours in the presence of Golgi Stop (0.75 µl/ml). Cells were then fixed with 4% paraformaldehyde solution and permeabilized in BSA-containing 0.1% Triton X-100/PBS. Permeabilized cells were stained for Foxp3-APC, Helios-PE, IL-2-PE and IFNγ-PECy7 (BD Bioscience).

Cell Proliferation and Suppression Assays

For standard suppression assays, fresh isolated or expanded T effectors were washed 2× in PBS and labeled with 10 µM eFluor-450 for 20 min. Labeled cells were washed in FBS-supplemented medium and $2-5\times10^4$ cells co-cultured with γ-irradiated DR1-PBMC as APCs in the presence of specific FVIII-2191-2220 or a non-specific peptide (OVA) for 4-5 days. Proliferation was measured by a flow cytometric dye-dilution assay.

An in vitro Treg suppression assay was also performed as previously described[5,6]. Briefly, 3-4 week-expanded 17195TCR-effectors ($4\times10^4$) and γ-irradiated DR1-PBMCs were mixed at a ratio of 1:2 in the absence of IL-2. 17195TCR-Tregs were then added at various ratios and stimulated with soluble anti-CD3 antibody (0.5 µg/ml), FVIII-2191-2220 (0.5 µg/ml), or rFVIII (0.2 µg/ml) for 4-6 days and cell proliferation was assayed by dye dilution or by thymidine incorporation following incubation with [$^3$H]-thymidine (1 µCi/well) during the final 16-18 hours of culture. To measure suppression of cytokine production by Tregs, T effectors were incubated with Tregs (mock or 17195TCR) for 24 hours in the presence of FVIII-2191-2220 with irradiated DR1-PBMC and without IL-2. The supernatants were harvested and assayed for cytokine expression using a Th1, Th2 and Th17 human CBA kit (BD Bioscience).

DNA Methylation Analysis of Human Treg-Specific De-Methylation Regions (TSDR)

Three-week-expanded 17195TCR-Tregs were harvested, washed and genomic DNA extracted using a Wizard Genomic DNA Purification Kit (Promega). Epitect Bisulfite kits (Qiagen) were used to convert unmethylated Cytosines in the genomic DNAs to Uracils. A Promark Q24 instrument was used to detect and quantify methylated TSDR CpGs in the TSDR, using human TSDR-specific primers. Nine CpGs were determined to be methylation-sensitive TSDR CpGs within the Foxp3 genome (−2376 to −2263 from translation starting site).

ELISPOT Assay and In Vitro Suppression of Antibody Production by FVIII-Specific B Cells from HLA-Transgenic Hemophilia a Mice To quantify the in vitro anti-FVIII suppression, "humanized" hemophilia A mice were created by crossing E16-FVIII knockout (KO) mice[7] with DR1-transgenic mice (Dr. Chella David, Mayo Clinic). These mice were immunized subcutaneously with 2 µg rFVIII in incomplete Freund's adjuvant and boosted twice with 2 µg rFVIII in PBS intraperitoneally 3 and 5 weeks later. Pooled splenocytes from two immunized mice having established titers against FVIII were used as T-responders. Next, $1\times10^7$ HLA-DR1-FVIII-KO splenocytes were co-cultured with 17195TCR-Tregs or mock transduced Tregs at various ratios in T25 flasks for 6 days in RPMI 1640 medium supplemented with 10% FBS, 2 mM L-glutamine, 50 µM 2-mercaptoethanol, and 1 µg/ml rFVIII. The effect of these human Tregs on FVIII-specific antibody secreting cell (ASC) formation was measured using an enzyme-linked immunospot (ELISPOT) assay with rFVIII-coated plates[8,9]. Cells were washed, added to ELISPOT wells in triplicate and cultured overnight. The captured anti-FVIII antibodies were detected by HRP-conjugated anti-mouse IgG (H+L) (Invitrogen), and anti-FVIII ASC revealed with AEC substrate (BD Biosciences). Plates were read on a CTL ELISPOT plate reader (Cellular Technology Limited, Shaker Heights, Ohio).

Figures 3A, 3B, 3C:
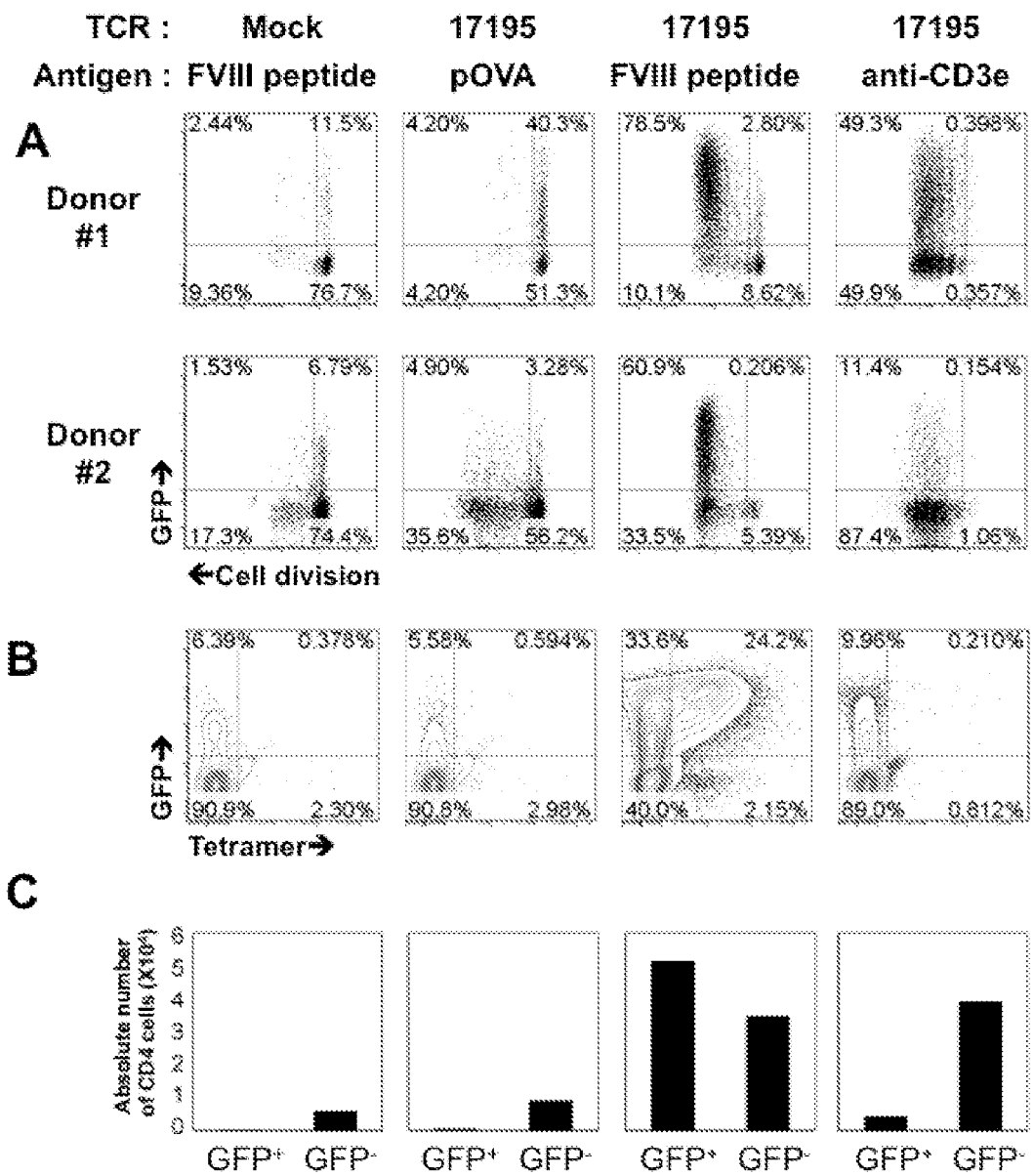
Figure 3D:
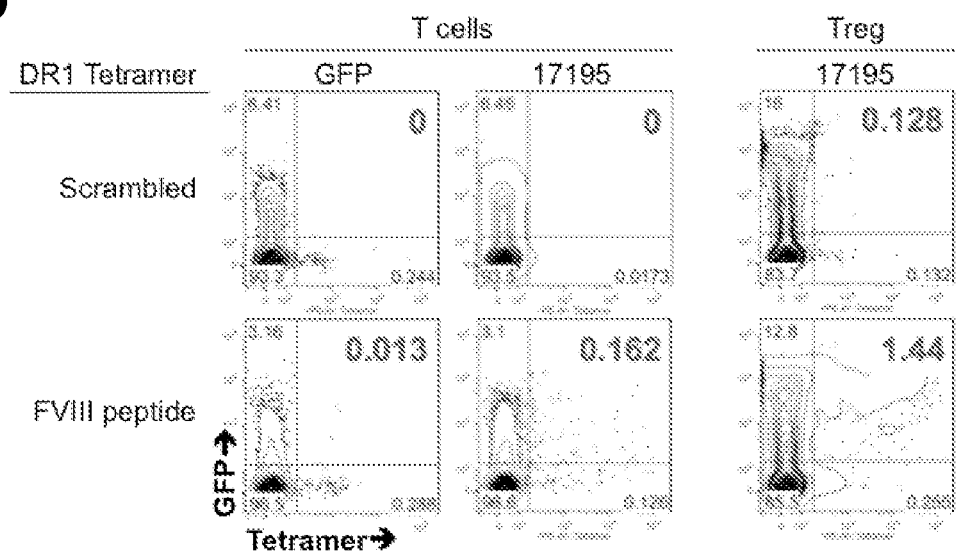
Figure 3E:
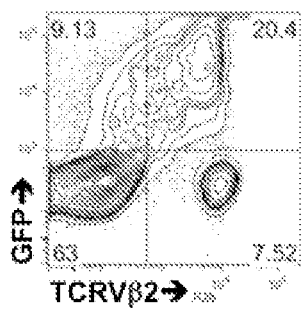
Figure 3F:
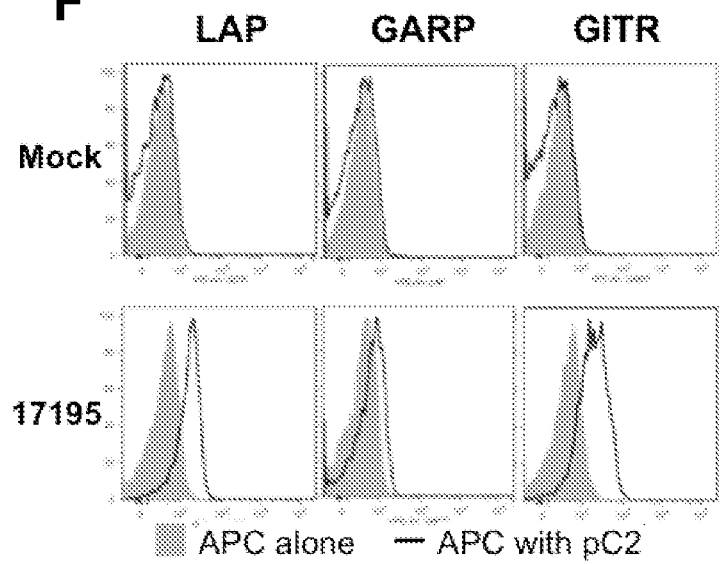

Retroviral Expression of an Engineered FVIII-Specific TCR and FVIII-Mediated Proliferation of Polyclonal CD4 T Effectors To prepare T effectors for retroviral transduction of 17195TCR, PBMCs from normal healthy donors were sorted to obtain a naïve CD4+ T population (CD4+CD25− CD127+CD45RA+); natural T-regulatory cells (nTreg, CD4+ CD25$^{hi}$CD127$^{low}$) were also sorted and transduced as described below, stimulated with plate-coated anti-CD3ε antibody and anti-CD28 antibody, and transduced with retroviral particles encoding the 17195TCR. Transduced cells were maintained and rested in the presence of IL-2 for 8 days without additional stimuli. Twenty-four hours after transduction, initial transfection efficiency was determined by measuring the GFP expression. GFP+ cells comprised 6-25% of the virus-treated CD4 cells, and this proportion did not change during the maintenance period (2-4 days) (Fig S1A and data not shown). Transduction yields were comparable for mock-transduced cells and 17195TCR-transduced T effectors. The transduced GFP+ CD4 cells were next stained with an anti-Vβ2 antibody (recognizing the 17195TCR). The GFP+ cells were predominantly Vβ2+ (67% of the GFP+ cells) whereas 10% of the non-transduced (GFP−) cells were Vβ2+, indicating endogenous TCR expression levels (FIG. 3E). The transduced cells showed GFP intensity that was proportional to the 17195TCR expression level.

To validate the antigen specificity of the 17195TCR, the transduced T effector cells were stained with DR1 tetramers loaded with FVIII-2191-2220. Despite the strong expression of this TCR on GFP+ cells, only a small percentage of expanded naïve T cells (less than 5% of the transduced and 0.2% of the total CD4 population) showed a tetramer+ phenotype (FIG. 3D), presumably due to pairing of the α and β chains with endogenous TCR chains. In spite of the low percentage of tetramer+17195 TCR-transduced cells, their tetramer+ staining intensity was more than ten-fold higher and distinguishable from the non-specific tetramer staining (0.41% of the transduced and 0.01% of the total naïve CD4+ population) or of mock-transduced cells (no tetramer+ cells). These results indicated that a subset of the primary CD4+ cells transduced with the 17195TCR expressed a TCR that recognized FVIII-2191-2220 presented on HLA-DR1.

The functional activity of these 17195TCR-transduced T effectors was tested directly as follows. Ten day-rested TCR-transduced CD4 cells were labeled with a cell proliferation dye, and a proliferation assay was performed with DR1-PBMC presenting FVIII-2191-2220 or an OVA peptide (pOVA). When 17195TCR-effectors were cultured with FVIII-2191-2220, almost 100% of the GFP+ cells proliferated (FIG. 3A) and the proportion of GFP+ cells increased to 61-81%, more than the non-proliferating cells. Expanded GFP+ 17195TCR T effectors bound specifically to DR1-tetramers loaded with FVIII-2191-2220:24% of 17195TCR T effectors were tetramer+ (FIG. 3B). These specifically stimulated 17195TCR T effector GFP+ cells expanded 50× more than those cultured with pOVA (FIG. 3C). Moreover, the increase in absolute cell count suggests that an initial stimulation with FVIII-2191-2220 efficiently enriched the specifically transduced T effector population.

Production of Antigen Specific Treg Cells and Induction of Treg-Specific Factors by Antigenic Stimulation To produce TCR17195 expressing T regulatory cell (Treg-17195), human Tregs (CD4+CD25$^{hi}$CD127$^{lo}$) were isolated from healthy donor's buffy coat. Pre-stimulation, retroviral transduction, and expansion of Treg-17195 was done as described above for effector T cells and as shown in FIG. 2. To address C2-specific Treg activation through TCR17195, expanded Treg-17195 cells were co-cultured with gamma-irradiated DR1-HLA typed PBMCs (6000 rad by Co60) for 24 hrs in the presence of pOVA, pFVIII C2, or soluble anti-CD3e antibody. Foxp3 and GARP (glycoprotein A repetitions predominant, LRRC32) staining was then done on fixed, co-cultured cells. Foxp3 and GARP are transiently induced at the early stage (24-48 hrs) of activated Tregs. In GFP negative population, the induction of Foxp3 and Helios was shown only in the anti-CD3e Ab stimulation group and pC2-mediated stimulation did not give any induction of Foxp3 and Helios (FIG. 4 dot plots and histograms in left box). In GFP positive cells (expressing the TCR), stimulation by C2 induced expression of Foxp3 and Helios in a portion of cells as well as stimulation by CD3e. See FIG. 4. The data clearly show C2-mediated TCR stimulation triggers activation of transduced Treg cells (dot plots and histograms in right box of FIG. 4).

Functional Stability of Transduced Tregs after Long-Term Ex Vivo Expansion Using Specific FT/III-2191-2220 and ODN The function of expanded human Tregs in vitro can be stabilized using random oligodeoxynucleotides (ODN)[10-13]. Thus, we hypothesized that long-term expansion in the presence of FVIII-2191-2220 and ODN would optimize the enrichment of antigen-specific, transduced Treg expressing high levels of Foxp3 and Helios. Transduced Tregs were cultured with anti-CD3ε antibody, FVIII-2191-2220, or FVIII-2191-2220 and ODN (FVIII-2191-2220/ODN), in the presence of DR1-PBMCs plus recombinant IL-2 (FIG. 10). After one round of expansion (8 days), the rate of cellular division slowed. The cell numbers and GFP fluorescence intensity after this expansion step were comparable in all groups (data not shown). Foxp3 and Helios in the GFP+ cells were well maintained at levels similar to those of freshly isolated Tregs (FIG. 11).

Figures 5A, 5B, 5C, 5D:
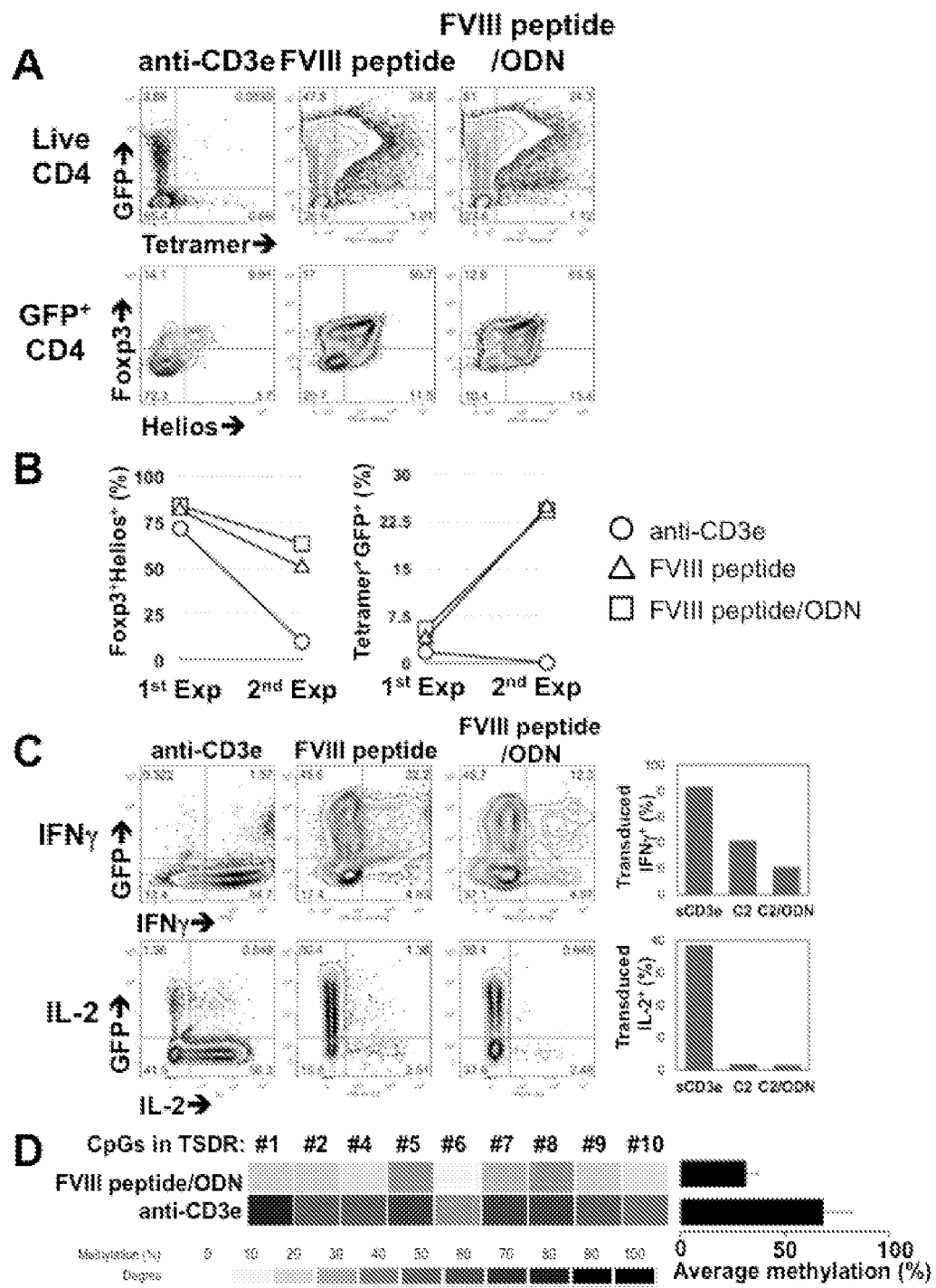

After a second round of expansion, GFP+ cells were dramatically enriched only in the FVIII-2191-2220 and FVIII-2191-2220/ODN culture conditions (72% and 74%), compared to anti-CD3ε stimulation (top dot plots in FIG. 5A). Moreover, the percentage of tetramer+ cells in the GFP+ cell population was increased in both FVIII-2191-2220 and FVIII-2191-2220/ODN conditions. Foxp3 and Helios expression after FVIII-2191-2220 stimulation showed a significantly different phenotype than of anti-CDR. Specifically expanded GFP+ cells maintained Foxp3 and Helios expression, but cells cultured with anti-CD3ε did not (bottom dot plots in FIG. 5A). The data in FIG. 5B suggest that the FVIII-2191-2220 signal given to 17195TCR Treg during expansion contributed to the enrichment of these FVIII-specific Tregs.

Analysis of the cytokine expression profile (FIG. 5C) showed that cells undergoing two rounds of expansion with FVIII-2191-2220/ODN had the lowest percentage of IFNγ (20%) versus anti-CD3 conditioned cells (80%) and FVIII-2191-2220 cells (40%) (top dot plots and graph in FIG. 5C). The FVIII-2191-2220 stimulated groups had few IL-2+ cells (bottom dot plots and graph in FIG. 5C). These results demonstrate that the FVIII-2191-2220/ODN co-treatment protocol stabilizes Foxp3 and Helios expression and prevents the conversion of Tregs to IFNγ-secreting T effectors.

The status of Treg-specific demethylated region (TSDR) in ex vivo expanded Foxp3+Helios+ human and murine nTregs is an important marker for stabilization of Tregs[13-17]. GFP+ cells were FACS-sorted from expanded 17195TCR Tregs and the methylation status of their TSDR CpGs analyzed (FIG. 5D). FVIII-2191-2220/ODN-conditioned Tregs showed well-preserved demethylation for each of the TSDR CpGs compared to anti-CD3ε conditioned GFP+ cells (FIG. 5D).

Evaluation of Suppressive Function

For the immunosuppression assay, naïve T effector cells and Tregs were prepared as in FIGS. 2-4. T naïve cells were expanded with C2 and irradiated antigen presenting cells (APC) after viral transduction of TCR17195 for 14 days and the expanded T effector-17195 population was used as responder cells. To monitor cell division of GFP positive cells, responders were labeled with the Cell Proliferation Dye-eFluor450 (CPD450). Tregs cells were transduced with mock virus or TCR17195, then were expanded for 14 days with anti-CD3e antibody or pC2 peptide. In the co-culture, the ratio of Responders to Stimulators was fixed at 1:1 and the amount of Tregs was varied as indicated in FIG. 6.

Cell mixtures were cultured with anti-CD3e antibody or pC2 for 2 days (FIG. 6 A) or 4 days (FIG. 6 B) without IL-2 addition. Treg-17195 produced C2-specific inhibition of division of the proliferation dye CPD450 labeled GFP+ responders (see FIG. 6 A). Treg-17195 produced C2-specific immunosuppression (see FIG. 6 B). To confirm and measure cell growth in mixed culture, [$^3$H]-thymidine was added at 18 hrs before harvest, with similar results.

Figure 6C:
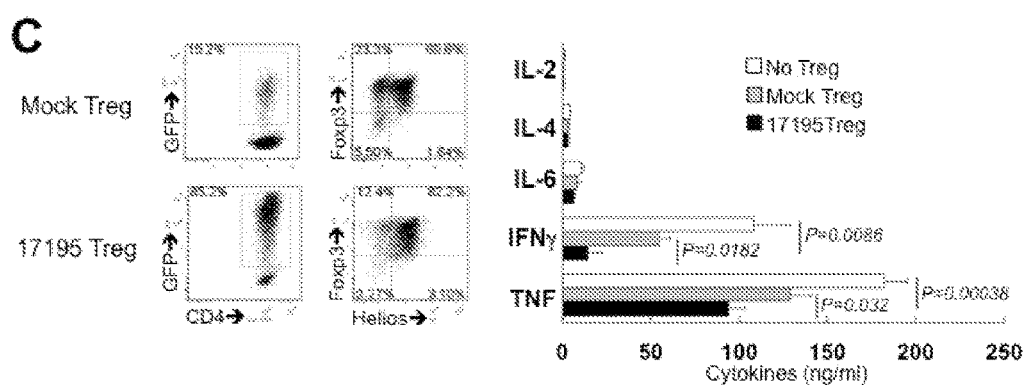

Since Tregs are known to inhibit the production of inflammatory cytokines[18-22], we next determined the levels of IL-2, IFNγ, IL-4, and IL-17 produced by T effectors in the presence of Tregs after 24 h. At a ratio of 1:8 (Tregs:T effectors), FVIII-specific Tregs significantly suppressed dominant Th1 cytokine (IFNγ and TNF) production by T effectors compared to mock Tregs (FIG. 6C). Interestingly, FVIII-specific IL-10 production was also reduced in a FVIII-specific Tregs-dependent manner.

Effective Suppression of FVIII-Specific ASC Formation by 17195TCR Tregs In Vitro To determine whether human FVIII-specific Tregs could suppress the humoral anti-FVIII response as well, splenocytes from FVIII-primed HLA-DR1-FVIII-KO mice were co-cultured with rFVIII plus 17195TCR-Tregs or mock-transduced Tregs at different ratios (FIG. 7). Specific 17195TCR-Tregs dramatically inhibited anti-FVIII ASC formation at all ratios of Tregs: total splenocytes. Mock-transduced Tregs did not suppress the anti-FVIII antibody response, but at high Tregs: total splenocytes ratios more ASC were detected, presumably due to cytokines produced from xenogeneic recognition. The almost complete suppression of ASC formation by 17195TCR-Tregs suggests involvement of both FVIII-specific and non-specific xenogeneic responses (FIG. 7). In summary, T cell receptor from a patient clone specific for human FVIII was expressed in expanded human T effector and natural T regulatory cells. These cells responded specifically to the FVIII peptide recognized by the original T cell clone and increased in both the number of tetramer binding cells and Treg markers. Tregs also specifically suppressed responder effector cells recognizing FVIII. Moreover, studies with an HLA-transgenic, FVIII-deficient mouse model demonstrated that antibody production by FVIII-specific B cells in vitro were profoundly inhibited in the presence of these FVIII-specific Tregs, thus validating their translational potential utility to treat anti-FVIII inhibitory antibody formation in hemophilia A patients.

The methods described herein therefore are useful for producing Tregs useful in a cellular therapy to treat hemophilia patients who are prone to making antibodies against FVIII that inhibit its clotting function, as well as in patients with type I diabetes, uveitis, and multiple sclerosis. Further, the methods can be applied to other diseases associated with undesirable immune responses.

REFERENCES

1. Wälchli S, Løset GÅ, Kumari S, et al. A practical approach to T-cell receptor cloning and expression. *PLoS ONE.* 2011; 6(11):e27930.
2. James E A, Kwok W W, Ettinger R A, Thompson A R, Pratt K P. T-cell responses over time in a mild hemophilia A inhibitor subject: epitope identification and transient immunogenicity of the corresponding self-peptide. *J. Thromb. Haemost.* 2007; 5(12):2399-2407.
3. Ettinger R A, James E A, Kwok W W, Thompson A R, Pratt K P. Lineages of human T-cell clones, including T helper 17/T helper 1 cells, isolated at different stages of anti-factor VIII immune responses. *Blood.* 2009; 114(7): 1423-1428.
4. Yang S, Cohen C J, Peng P D, et al. Development of optimal bicistronic lentiviral vectors facilitates high-level TCR gene expression and robust tumor cell recognition. *Gene Ther.* 2008; 15(21):1411-1423.
5. Thornton A M, Piccirillo C A, Shevach E M. Activation requirements for the induction of CD4+CD25+ T cell suppressor function. *Eur J Immunol.* 2004; 34(2):366-376.
6. Thornton A M, Donovan E E, Piccirillo C A, Shevach E M. Cutting edge: IL-2 is critically required for the in vitro activation of CD4+CD25+ T cell suppressor function. *J Immunol.* 2004; 172(11):6519-6523.
7. Bi L, Lawler A M, Antonarakis S E, et al. Targeted disruption of the mouse factor VIII gene produces a model of haemophilia A. *Nat. Genet.* 1995; 10(1):119-121.
8. Hausl C, Ahmad R U, Sasgary M, et al. High-dose factor VIII inhibits factor VIII-specific memory B cells in hemophilia A with factor VIII inhibitors. *Blood.* 2005; 106(10): 3415-3422.
9. Hausl C, Ahmad R U, Schwarz H P, et al. Preventing restimulation of memory B cells in hemophilia A: a potential new strategy for the treatment of antibody-dependent immune disorders. *Blood.* 2004; 104(1):115-122.
10. Vonderheide R H, June C H. Engineering T cells for cancer: our synthetic future. *Immunol. Rev.* 2014; 257(1): 7-13.
11. Grupp S A, Kalos M, Barrett D, et al. Chimeric antigen receptor-modified T cells for acute lymphoid leukemia. *N Engl J Med.* 2013; 368(16):1509-1518.
12. Kalos M, June C H. Adoptive T Cell Transfer for Cancer Immunotherapy in the Era of Synthetic Biology. *Immunity.* 2013; 39(1):49-60.
13. Kim Y C, Bhairavabhotla R, Yoon J, et al. Oligodeoxynucleotides stabilize Helios-expressing Foxp3+ human T regulatory cells during in vitro expansion. *Blood.* 2012; 119(12):2810-2818.
14. Fransson M, Piras E, Burman J, et al. CAR/FoxP3-engineered T regulatory cells target the CNS and suppress EAE upon intranasal delivery. *J Neuroinflammation.* 2012; 9:112-112.
15. Jethwa H, Adami A A, Maher J. Use of gene-modified regulatory T-cells to control autoimmune and alloimmune pathology: Is now the right time? *Clinical Immunology.* 2014; 150(1):51-63.

16. Floess S, Freyer J, Siewert C, et al. Epigenetic control of the foxp3 locus in regulatory T cells. *PLoS Biol.* 2007; 5(2):e38.

17. Polansky J K, Kretschmer K, Freyer J, et al. DNA methylation controls Foxp3 gene expression. *Eur J Immunol.* 2008; 38(6):1654-1663.

```
                        SEQUENCE LISTING

<160> NUMBER OF SEQ ID NOS: 12

<210> SEQ ID NO 1
<211> LENGTH: 602
<212> TYPE: PRT
<213> ORGANISM: Homo sapiens

<400> SEQUENCE: 1

Arg Gln Val Ala Arg Val Ile Val Phe Leu Thr Leu Ser Thr Leu Ser
1               5                   10                  15

Leu Ala Lys Thr Thr Gln Pro Ile Ser Met Asp Ser Tyr Glu Gly Gln
                20                  25                  30

Glu Val Asn Ile Thr Cys Ser His Asn Asn Ile Ala Thr Asn Asp Tyr
            35                  40                  45

Ile Thr Trp Tyr Gln Gln Phe Pro Ser Gln Gly Pro Arg Phe Ile Ile
        50                  55                  60

Gln Gly Tyr Lys Thr Lys Val Thr Asn Glu Val Ala Ser Leu Phe Ile
65                  70                  75                  80

Pro Ala Asp Arg Lys Ser Ser Thr Leu Ser Leu Pro Arg Val Ser Leu
                85                  90                  95

Ser Asp Thr Ala Val Tyr Tyr Cys Leu Val Gly Asp Ala Pro Asn Ser
                100                 105                 110

Gly Asn Thr Pro Leu Val Phe Gly Lys Gly Thr Arg Leu Ser Val Ile
            115                 120                 125

Ala Asn Ile Gln Asn Pro Asp Pro Ala Val Tyr Gln Leu Arg Asp Ser
        130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
                180                 185                 190

Ala Trp Ser Asn Lys Ser Asp Phe Ala Cys Ala Asn Ala Phe Asn Asn
            195                 200                 205

Ser Ile Ile Pro Glu Asp Thr Phe Phe Pro Ser Pro Glu Ser Ser Cys
        210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser Arg Ala
                260                 265                 270

Lys Arg Gly Ser Gly Ala Thr Asn Phe Ser Leu Leu Lys Gln Ala Gly
            275                 280                 285

Asp Val Glu Glu Asn Pro Gly Pro Met Leu Leu Leu Leu Leu Leu Leu
        290                 295                 300

Gly Pro Gly Ser Gly Leu Gly Ala Val Val Ser Gln His Pro Ser Arg
305                 310                 315                 320

Val Ile Cys Lys Ser Gly Thr Ser Val Lys Ile Glu Cys Arg Ser Leu
                325                 330                 335

Asp Phe Gln Ala Thr Thr Met Phe Trp Tyr Arg Gln Phe Pro Lys Lys
```

```
            340                 345                 350
Ser Leu Met Leu Met Ala Thr Ser Asn Glu Gly Ser Lys Ala Thr Tyr
            355                 360                 365

Glu Gln Gly Val Glu Lys Asp Lys Phe Leu Ile Asn His Ala Ser Leu
        370                 375                 380

Thr Leu Ser Thr Leu Thr Val Thr Ser Ala Gln Pro Glu Asp Ser Ser
385                 390                 395                 400

Phe Tyr Ile Cys Ser Ala His Thr Arg Ala Asn Tyr Gly Tyr Thr Phe
                405                 410                 415

Gly Ser Gly Thr Arg Leu Thr Val Val Glu Asp Leu Asn Lys Val Phe
            420                 425                 430

Pro Pro Glu Val Ala Val Phe Glu Pro Ser Glu Ala Glu Ile Ser His
            435                 440                 445

Thr Gln Lys Ala Thr Leu Val Cys Leu Ala Thr Gly Phe Phe Pro Asp
        450                 455                 460

His Val Glu Leu Ser Trp Trp Val Asn Gly Lys Glu Val His Ser Gly
465                 470                 475                 480

Val Ser Thr Asp Pro Gln Pro Leu Lys Glu Gln Pro Ala Leu Asn Asp
                485                 490                 495

Ser Arg Tyr Cys Leu Ser Ser Arg Leu Arg Val Ser Ala Thr Phe Trp
            500                 505                 510

Gln Asn Pro Arg Asn His Phe Arg Cys Gln Val Gln Phe Tyr Gly Leu
        515                 520                 525

Ser Glu Asn Asp Glu Trp Thr Gln Asp Arg Ala Lys Pro Val Thr Gln
530                 535                 540

Ile Val Ser Ala Glu Ala Trp Gly Arg Ala Asp Cys Gly Phe Thr Ser
545                 550                 555                 560

Val Ser Tyr Gln Gln Gly Val Leu Ser Ala Thr Ile Leu Tyr Glu Ile
                565                 570                 575

Leu Leu Gly Lys Ala Thr Leu Tyr Ala Val Leu Val Ser Ala Leu Val
            580                 585                 590

Leu Met Ala Met Val Lys Arg Lys Asp Phe
            595                 600

<210> SEQ ID NO 2
<211> LENGTH: 618
<212> TYPE: PRT
<213> ORGANISM: Homo sapiens

<400> SEQUENCE: 2

Glu Thr Leu Leu Gly Val Ser Leu Val Ile Leu Trp Leu Gln Leu Ala
1               5                   10                  15

Arg Val Asn Ser Gln Gln Gly Glu Glu Asp Pro Gln Ala Leu Ser Ile
            20                  25                  30

Gln Glu Gly Glu Asn Ala Thr Met Asn Cys Ser Tyr Lys Thr Ser Ile
        35                  40                  45

Asn Asn Leu Gln Trp Tyr Arg Gln Asn Ser Gly Arg Gly Leu Val His
50                  55                  60

Leu Ile Leu Ile Arg Ser Asn Glu Arg Glu Lys His Ser Gly Arg Leu
65                  70                  75                  80

Arg Val Thr Leu Asp Thr Ser Lys Lys Ser Ser Ser Leu Leu Ile Thr
                85                  90                  95

Ala Ser Arg Ala Ala Asp Thr Ala Ser Tyr Phe Cys Ala Thr Asp Thr
            100                 105                 110
```

-continued

Thr Ser Gly Thr Tyr Lys Tyr Ile Phe Gly Thr Gly Thr Arg Leu Lys
        115                 120                 125

Val Leu Ala Asn Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

Arg Ala Lys Arg Gly Ser Gly Ala Thr Asn Phe Ser Leu Leu Lys Gln
        275                 280                 285

Ala Gly Asp Val Glu Glu Asn Pro Gly Pro Met Leu Leu Leu Leu
        290                 295                 300

Leu Leu Gly Pro Gly Ile Ser Leu Leu Leu Pro Gly Ser Leu Ala Gly
305                 310                 315                 320

Ser Gly Leu Gly Ala Val Val Ser Gln His Pro Ser Trp Val Ile Cys
                325                 330                 335

Lys Ser Gly Thr Ser Val Lys Ile Glu Cys Arg Ser Leu Asp Phe Gln
            340                 345                 350

Ala Thr Thr Met Phe Trp Tyr Arg Gln Phe Pro Lys Gln Ser Leu Met
        355                 360                 365

Leu Met Ala Thr Ser Asn Glu Gly Ser Lys Ala Thr Tyr Glu Gln Gly
370                 375                 380

Val Glu Lys Asp Lys Phe Leu Ile Asn His Ala Ser Leu Thr Leu Ser
385                 390                 395                 400

Thr Leu Thr Val Thr Ser Ala His Pro Glu Asp Ser Ser Phe Tyr Ile
                405                 410                 415

Cys Ser Ala Arg Asp Leu Thr Ser Gly Ser Leu Asn Glu Gln Phe Phe
            420                 425                 430

Gly Pro Gly Thr Arg Leu Thr Val Leu Glu Asp Leu Asn Lys Val Phe
        435                 440                 445

Pro Pro Glu Val Ala Val Phe Glu Pro Ser Glu Ala Glu Ile Ser His
450                 455                 460

Thr Gln Lys Ala Thr Leu Val Cys Leu Ala Thr Gly Phe Phe Pro Asp
465                 470                 475                 480

His Val Glu Leu Ser Trp Trp Val Asn Gly Lys Glu Val His Ser Gly
                485                 490                 495

Val Ser Thr Asp Pro Gln Pro Leu Lys Glu Gln Pro Ala Leu Asn Asp
            500                 505                 510

Ser Arg Tyr Cys Leu Ser Ser Arg Leu Arg Val Ser Ala Thr Phe Trp
        515                 520                 525

Gln Asn Pro Arg Asn His Phe Arg Cys Gln Val Gln Phe Tyr Gly Leu

```
Ser Glu Asn Asp Glu Trp Thr Gln Asp Arg Ala Lys Pro Val Thr Gln
545                 550                 555                 560

Ile Val Ser Ala Glu Ala Trp Gly Arg Ala Asp Cys Gly Phe Thr Ser
                565                 570                 575

Val Ser Tyr Gln Gln Gly Val Leu Ser Ala Thr Ile Leu Tyr Glu Ile
            580                 585                 590

Leu Leu Gly Lys Ala Thr Leu Tyr Ala Val Leu Val Ser Ala Leu Val
        595                 600                 605

Leu Met Ala Met Val Lys Arg Lys Asp Phe
    610                 615
```

```
<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (8)..(9)
<223> OTHER INFORMATION: Inosine
<220> FEATURE:
<221> NAME/KEY: modified_base
<222> LOCATION: (13)..(14)
<223> OTHER INFORMATION: Inosine
<220> FEATURE:
<221> NAME/KEY: modified_base
<222> LOCATION: (18)..(19)
<223> OTHER INFORMATION: Inosine

<400> SEQUENCE: 3
caccgggnng ggnngggnn                                                19

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agtcagattt gttgctccag gcc                                           23

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttcacccacc agctcagctc c                                             21

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
```

```
<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atacgcgtag atctctgctt ctgatggc                                            28

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tttttttttt                                                                10

<210> SEQ ID NO 9
<211> LENGTH: 16
<212> TYPE: PRT
<213> ORGANISM: Homo sapiens

<400> SEQUENCE: 9

Cys Leu Val Gly Asp Ala Pro Asn Ser Gly Asn Thr Pro Leu Val Phe
1               5                   10                  15

<210> SEQ ID NO 10
<211> LENGTH: 13
<212> TYPE: PRT
<213> ORGANISM: Homo sapiens

<400> SEQUENCE: 10

Cys Ser Ala His Thr Arg Ala Asn Tyr Gly Tyr Thr Phe
1               5                   10

<210> SEQ ID NO 11
<211> LENGTH: 14
<212> TYPE: PRT
<213> ORGANISM: Homo sapiens

<400> SEQUENCE: 11

Cys Ala Thr Asp Thr Thr Ser Gly Thr Tyr Lys Tyr Ile Phe
1               5                   10

<210> SEQ ID NO 12
<211> LENGTH: 16
<212> TYPE: PRT
<213> ORGANISM: Homo sapiens

<400> SEQUENCE: 12

Cys Ser Ala Arg Asp Leu Thr Ser Gly Ser Leu Asn Glu Gln Phe Phe
1               5                   10                  15
```

(atacgcgttc tctcagctgg tacacgg 27 — continued from previous page)

What is claimed is:

1. An antigen specific T regulatory cell expressing a T cell receptor that specifically recognizes an antigen associated with hemophilia or multiple sclerosis, wherein, when the antigen is associated with hemophilia the T cell receptor specifically recognizes the C2 domain of human clotting factor VIII and has the sequence of SEQ ID NO: 1, and when the antigen is associated with multiple sclerosis the T cell receptor specifically recognizes myelin basic protein (MBP) and has the sequence of SEQ ID NO: 2.

2. The antigen specific T regulatory cell of claim 1, wherein the antigen specific T regulatory cell expresses a T cell receptor that specifically recognizes the C2 domain of human clotting factor VIII and has the sequence of SEQ ID NO: 1.

3. The antigen specific T regulatory cell of claim 1, wherein the antigen specific T regulatory cell expresses a T cell receptor that specifically recognizes myelin basic protein (MBP) and has the sequence of SEQ ID NO: 2.

4. A method for expanding an antigen specific T regulatory cell according to claim 1, the method comprising culturing the cell in IL-2 containing RPMI1640 media with 10% fetal bovine serum for up to 4 days.

5. A method for expanding a functionally stable antigen specific T regulatory cell according to claim 1, the method comprising culturing the cell in the presence of the specific antigen recognized by the T cell receptor and further in the presence of oligodeoxynucleotides, irradiated DR1 HLA-typed peripheral blood mononuclear cells, and IL2.

6. The method of claim 5, wherein the cell is cultured for about 21 days.

7. An antigen specific T regulatory cell transduced with an expression vector comprising a nucleotide sequence encoding a T cell receptor having the sequence of SEQ ID NO:1 or SEQ ID NO:2.

8. The antigen specific T regulatory cell of claim 7, wherein the T regulatory cell is transduced with an expression vector comprising a nucleotide sequence encoding a T cell receptor having the sequence of SEQ ID NO:1.

9. The antigen specific T regulatory cell of claim 7, wherein the T regulatory cell is transduced with an expression vector comprising a nucleotide sequence encoding a T cell receptor having the sequence of SEQ ID NO:2.

10. A method of reducing an immune response to myelin basic protein (MBP), comprising administering to a subject in need thereof a composition comprising an antigen specific T regulatory cell according to claim 9.

11. The method of claim 10, wherein the subject is suffering from multiple sclerosis.

12. A method of reducing an immune response to human clotting factor VIII, comprising administering to a subject in need thereof a composition comprising an antigen specific T regulatory cell according to claim 7, wherein the T regulatory cell is transduced with an expression vector comprising a nucleotide sequence encoding a T cell receptor having the sequence of SEQ ID NO:1.

13. The method of claim 12, wherein the subject is suffering from hemophilia.

14. The method of claim 12, wherein the subject has received a biotherapeutic treatment for hemophilia.

15. A method for producing an antigen specific T regulatory cell of claim 7, wherein the T regulatory cell is capable of specifically suppressing an immune response to an antigen associated with hemophilia or multiple sclerosis, comprising:

transducing a T regulatory cell with an expression vector comprising a nucleotide sequence encoding a T cell receptor that specifically recognizes an antigen associated with hemophilia or multiple sclerosis, wherein, when the antigen is associated with hemophilia the T cell receptor specifically recognizes the C2 domain of human clotting factor VIII and has the sequence of SEQ ID NO: 1, and when the antigen is associated with multiple sclerosis the T cell receptor specifically recognizes myelin basic protein (MBP) and has the sequence of SEQ ID NO: 2; and expanding the transduced T regulatory cells ex vivo.

16. The method of claim 15, wherein the step of transducing a T regulatory cell comprises transducing an HLA-restricted natural T regulatory cell.

17. The method of claim 15, wherein the step of transducing a T regulatory cell comprises transducing a T regulatory cell with an amphotrophic packaging retrovirus.

18. The method of claim 15, wherein the T regulatory cell is obtained from a donor's buffy coat prior to being transduced.

19. The method of claim 15, wherein the T regulatory cell is subjected to a stimulation step prior to being transduced.

20. The method of claim 15, wherein the T cell receptor specifically recognizes the C2 domain of human clotting factor VIII and has the sequence of SEQ ID NO: 1.

21. The method of claim 15, wherein the T cell receptor specifically recognizes myelin basic protein (MBP) and has the amino acid sequence of SEQ ID NO: 2.

* * * * *